United States Patent
Sullivan et al.

(10) Patent No.: US 12,350,276 B2
(45) Date of Patent: Jul. 8, 2025

(54) METHODS FOR THE TREATMENT OF CANCER USING 1-(4-{[4-(DIMETHYLAMINO)PIPERIDIN-1-YL]CARBONYL}PHENYL)-3-[4-(4,6-DIMORPHOLIN-4-YL-1,3,5-TRIAZIN-2-YL)PHENYL]UREA

(71) Applicant: Celcuity Inc., Minneapolis, MN (US)

(72) Inventors: Brian Francis Sullivan, Medina, MN (US); Lance Gavin Laing, Orono, MN (US)

(73) Assignee: Celcuity Inc., Minneapolis, MN (US)

( * ) Notice: Subject to any disclaimer, the term of this patent is extended or adjusted under 35 U.S.C. 154(b) by 37 days.

(21) Appl. No.: 17/872,721

(22) Filed: Jul. 25, 2022

(65) Prior Publication Data

US 2023/0022525 A1    Jan. 26, 2023

Related U.S. Application Data

(60) Provisional application No. 63/285,327, filed on Dec. 2, 2021, provisional application No. 63/225,707, filed on Jul. 26, 2021.

(51) Int. Cl.
*A61K 31/5377* (2006.01)
*A61K 31/4196* (2006.01)
*A61K 31/519* (2006.01)
*A61K 31/566* (2006.01)
*A61P 35/04* (2006.01)

(52) U.S. Cl.
CPC ...... *A61K 31/5377* (2013.01); *A61K 31/4196* (2013.01); *A61K 31/519* (2013.01); *A61K 31/566* (2013.01); *A61P 35/04* (2018.01)

(58) Field of Classification Search
CPC ............ A61K 31/5377; A61K 31/4196; A61K 31/519; A61K 31/566; A61P 35/04
See application file for complete search history.

(56) References Cited

FOREIGN PATENT DOCUMENTS

WO    WO-2020076432 A1 *  4/2020  ........... A61K 31/138

OTHER PUBLICATIONS

G. Shapiro et al. (First-in-Human Study of PF-05212384 (PKI-587), a Small-Molecule, Intravenous, Dual Inhibitor of PI3K and mTOR in Patients with Advanced Cancer. Clin Cancer Res. Apr. 15, 2015;21(8):1888-95. doi: 10.1158/1078-0432.CCR-14-1306. (Year: 2015).*
Colombo I. et al., "Phase I dose-escalation study of the dual PI3K/mTORC1/2 inhibitor Gedatolisib (PF-05212384) in combination with paclitaxel (P) and carboplatin (C) in patients (pts) with advanced solid tumours," Annals of Oncology—Abstract Book of the ESMO Virtual Congress, vol. 31(Supplement 4) (2020).
Forero A. et al., "Phase Ib study to assess the safety, tolerability, and clinical activity of gedatolisib in combination with palbociclib and either letrozole or fulvestrant in women with metastatic or locally advanced/recurrent breast cancer, (B2151009)," Cancer Research, American Association for Cancer Research Inc. NLD, vol. 78(4) (Supplement 1) Abstract Only (2018).
Forero-Torres A. et al., "Phase Ib study of gedatolisib in combination with palbociclib and endocrine therapy (ET) in women with estrogen receptor (ER) positive (+) metastatic breast cancer (MBC) (B2151009)," Journal of Clinical Oncology, vol. 36 (15)(Supplement 1):3 pages Abstract only (2018).
International Search Report and Written Opinion, PCT/US2022/038188, dated Oct. 28, 2022, 8 pages.
Vargaftig J. et al., "Phase 2 Trial of Single Agent Gedatolisib (PF-05212384), a Dual PI3K/mTOR Inhibitor, for Adverse Prognosis and Relapse/Refractory AML: Clinical and Transcriptomic Results," Blood,vol. 132(1):5233 (2018).
Finn, R. et al., "Palbociclib and Letrozole in Advanced Breast Cancer," The New England Journal of Medicine, vol. 375(20):1925-1936 (2016).
Goetz, M. et al., "Monarch 3: Abemaciclib as Initial Therapy for Advanced Breast Cancer," Journal of Clinical Oncology, vol. 35(32):13 pages (2017).
Hortobagyi, G.N. et al., "Ribociclib as First-Line Therapy for HR-Positive, Advanced Breast Cancer," The New England Journal of Medicine, vol. 375(18):1738-1748 (2016).
Llombart-Cussac, A. et al., "Fulvestrant-Palbociclib vs Letrozole-Palbociclib as Initial Therapy for Endocrine-Sensitive, Hormone Receptor-Positive, ERBB2-Negative Advanced Breast Cancer a Randomized Clinical Trial," JAMA Oncology , vol. 7(12):1791-1799, doi: 10.1001/jamaoncol.2021.4301. (2021).
Turner, M. et al., "Palbociclib in Hormone-Receptor-Positive Advanced Breast Cancer," The New England Journal of Medicine, vol. 373(3): 209-219 (2015).

* cited by examiner

*Primary Examiner* — James H Alstrum-Acevedo
*Assistant Examiner* — Manahil Mirghani Ali Abdalhameed
(74) *Attorney, Agent, or Firm* — Nelson Mullins Riley & Scarborough LLP; Jane E. Remillard, Esq.; Catherine J. Kara, Esq.

(57) ABSTRACT

Provided are methods of treating cancer in a human subject. The method includes selecting a subject in need of treatment of cancer; administering to the subject a therapeutically effective amount of gedatolisib at least once a week for a period of three weeks; discontinuing administration of gedatolisib for a period of one week; and resuming administration of gedatolisib at least once a week following the period of discontinuation. The administration for at least a period of three weeks and discontinued administration for at least a period of one week constitutes a cycle, where the cycle is repeated for at least two cycles.

29 Claims, No Drawings

METHODS FOR THE TREATMENT OF CANCER USING 1-(4-{[4-(DIMETHYLAMINO)PIPERIDIN-1-YL]CARBONYL}PHENYL)-3-[4-(4,6-DIMORPHOLIN-4-YL-1,3,5-TRIAZIN-2-YL)PHENYL]UREA

RELATED APPLICATIONS

This application claims priority to U.S. Provisional Application No. 63/225,707, filed Jul. 26, 2021, and U.S. Provisional Application No. 63/285,327 filed Dec. 2, 2021. The entire contents of the prior applications are hereby incorporated by reference in their entirety.

FIELD OF THE INVENTION

The present invention relates to methods for treating cancer in a patient by administering 1-(4-{[4-(Dimethylamino)piperidin-1-yl]carbonyl}phenyl)-3-[4-(4,6-dimorpholin-4-yl-1,3,5-triazin-2-yl)phenyl]urea.

BACKGROUND 1-(4-{[4-(Dimethylamino)piperidin-1-yl]carbonyl}phenyl)-3-[4-(4,6-dimorpholin-4-yl-1,3,5-triazin-2-yl)phenyl]urea, also known as gedatolisib, has the chemical structure:

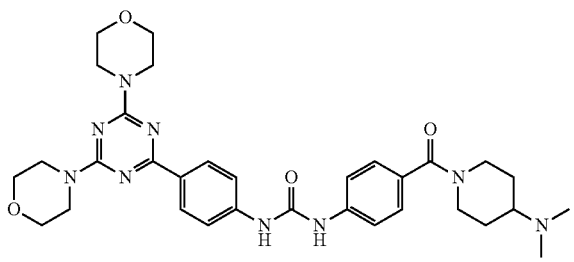

1-(4-{[4-(dimethylamino)piperidin-1-yl]carbonyl}phenyl)-3-[4-(4,6-dimorpholin-4-yl-1,3,5-triazin-2-yl)phenyl]urea 1-(4-{[4-(Dimethylamino)piperidin-1-yl]carbonyl}phenyl)-3-[4-(4,6-dimorpholin-4-yl-1,3,5-triazin-2-yl)phenyl]urea is an inhibitor of PI3 kinase and mTOR that is useful for the treatment of cancer. Mammalian Target of Rapamycin (mTOR) is a cell-signaling protein that regulates the response of tumor cells to nutrients and growth factors, as well as controlling tumor blood supply through effects on Vascular Endothelial Growth Factor (VEGF). Inhibitors of mTOR starve cancer cells and shrink tumors by inhibiting the effect of mTOR. All mTOR inhibitors bind to the mTOR kinase. This has at least two important effects. First, mTOR is a downstream mediator of the PI3K/Akt pathway. The PI3K/Akt pathway is thought to be over activated in numerous cancers and may account for the widespread response from various cancers to mTOR inhibitors. The over-activation of the upstream pathway would normally cause mTOR kinase to be over activated as well. However, in the presence of mTOR inhibitors, this process is blocked. The blocking effect prevents mTOR from signaling to downstream pathways that control cell growth. Over-activation of the PI3K/Akt kinase pathway is frequently associated with mutations in the PTEN gene, which is common in many cancers and may help predict what tumors will respond to mTOR inhibitors. The second major effect of mTOR inhibition is anti-angiogenesis, via the lowering of VEGF levels.

Breast cancer is the most common form of cancer and the leading cause of cancer death in women worldwide. Today the systemic treatment of breast cancer offers three major different treatment modalities and the applicability of these different treatment options is substantially dependent on the receptor status of the patient (Bernard-Marty et al., 2004). Endocrine and biological therapy requires the presence of the respective receptors on the cancer cells, whereas cytotoxic chemotherapy is independent of those specified receptors.

In patients with hormone-receptor-positive (HR+), Human Epidermal Growth Factor Receptor 2-negative (HER2−) breast cancer, endocrine therapy alone or in combination with cyclin dependent kinase 4 and 6 (CDK4/6) inhibitors, PI3K-a inhibitors, or mTOR inhibitors are usually the treatment of choice (NCCN Treatment Guidelines for Breast Cancer, 2021).

Selective ER modulators (tamoxifen), selective ER degrader (fulvestrant), and aromatase inhibitors (AIs) are established standards of care in women with HR+/HER2- metastatic breast cancer (mBC). The choice between these regimens when treating mBC depends on the type and duration of prior endocrine therapy treatment as well as the time elapsed from the end of prior endocrine therapy. Besides the well-known efficacy of these treatments as first-line therapies in women without visceral crisis, most patients develop endocrine resistance leading to therapeutic failure. Primary endocrine resistance is defined as relapse during the first two years of prior endocrine therapy or progressive disease within the first six months of first-line endocrine therapy for mBC. Secondary resistance is present (1) when a relapse occurs after the first two years of adjuvant endocrine therapy; (2) when a relapse occurs within 12 months of completing adjuvant endocrine therapy; or (3) when a progressive disease occurs after more than six months from the beginning of endocrine therapy for mBC.

Several mechanisms are responsible for endocrine resistance, including the dysregulation of multiple components of the ER pathway (aberration in ER expression, overexpression of ER co-activators, and down-regulation of co-repressors), altered regulation of signaling molecules involved in cell cycle or cell survival, and the activation of escape pathways that can provide cell replication.

One common mechanism of resistance to endocrine therapies is the activation of the cyclin-dependent kinases 4 and 6 (CDK4/6) pathway. These kinases drive cell cycle progression and division. Inhibiting activation of the CDK4/6 prevents estrogen from activating the cyclin D1-CDK4/6-Rb complex, thus blockading an important mechanism of resistance to endocrine therapies. The resulting cell cycle arrest induces a significant delay in tumor progression.

CDK 4/6 inhibitors were first introduced in 2015. Endocrine therapies administered in combination with oral CDK4/6 inhibitors lead to improved clinical efficacy when compared with endocrine therapies as monotherapy. In two randomized, double-blind clinical trials, treatment of HR+/HER2− advanced breast cancer patients with a combination of palbociclib and either letrozole or fulvestrant demonstrated a significant increase in the median progression free survival (PFS) period for patients who received palbociclib in combination with either letrozole or fulvestrant compared to patients who received letrozole or fulvestrant as single agents (Turner et al., N. Engl. J. Med. 373:209-19 (2015);

Finn et al., N. Engl. J. Med. 375:1925-36 (2016). These patients had previously progressed on or after prior endocrine therapy.

Another common mechanism of resistance to endocrine inhibitors is the activation of the PI3K pathway, an important intracellular pathway that regulates cell growth and metabolism. Approximately one third of HR+ breast cancer tumors resistant to endocrine therapy harbor activating mutations of the catalytic subunit of PI3K, referred to as PIK3CA. Fulvestrant used in combination with alpelisib, an oral PI3K-a inhibitor approved by the FDA in May 2019, has demonstrated improved clinical efficacy in patients whose tumors had a PIK3CA mutation and had not yet received treatment with a CDK4/6 inhibitor. These patients had previously progressed on or after prior endocrine therapy.

Similar to CDK4/6 and PI3K, the mTOR pathway has also been identified as a mechanism of resistance to endocrine therapy. Everolimus is an mTOR inhibitor that is currently approved by the FDA for the treatment of HR+/HER2- advanced breast cancer in combination with exemestane, an AI. Everolimus has also shown clinical benefit in combination with fulvestrant. These patients had previously progressed on or after prior AI therapy.

Despite the availability of new therapeutic options, women with HR+/HER2- breast cancer, particularly those whose cancer has metastasized to other organs and who are resistant to endocrine therapies, still face a poor long-term prognosis. Thus, there exists a need for a breast cancer treatment in patients that have not been successfully treated with endocrine therapy.

SUMMARY

Provided herein are methods of treating cancer in a patient. The method includes administering to the patient gedatolisib intravenously once weekly for three weeks, followed by one week when gedatolisib is not administered. This administration regimen, which constitutes a 28-day cycle (three weekly doses of gedatolisib followed by one week without gedatolisib), is then repeated as necessary. The cyclic administration of gedatolisib using the three weeks on, one week off cycle has shown to be more successful in the treatment of cancer than the administration of gedatolisib in a weekly, or non-cyclic manner.

Accordingly, in one aspect, the invention relates to a method of treating cancer in a human subject. The method includes selecting a human subject in need of treatment of cancer; administering to the human subject a therapeutically effective amount of gedatolisib, or a pharmaceutically acceptable salt, solvate, or ester thereof, at least once a week for a period of three weeks; discontinuing administration of gedatolisib, or pharmaceutically acceptable salt, solvate, or ester thereof, for a period of one week; and resuming administration of gedatolisib, or pharmaceutically acceptable salt, solvate, or ester thereof, at least once a week following the period of discontinuation. The administration for at least a period of three weeks and discontinued administration for at least a period of one week constitutes a cycle, and the cycle is repeated for at least two cycles.

In some embodiments, the resumed administration of gedatolisib, or pharmaceutically acceptable salt, solvate, or ester thereof, occurs at least once a week for a period of three weeks. The cycle of administration may occur for at least 3 cycles, at least 4 cycles, at least 5 cycles, at least 6 cycles, at least 7 cycles, at least 8 cycles, at least 9 cycles or at least 10 or more cycles. In further embodiments, the gedatolisib, or pharmaceutically acceptable salt, solvate, or ester thereof, is administered at a dose of 180 mg once a week.

In some embodiments, the method includes co-administering a CDK 4/6 inhibitor to the human subject at least once a week for a period of three weeks; discontinuing administration of the CDK 4/6 inhibitor for a period of one week; and resuming administration of the CDK 4/6 inhibitor for at least one week following the period of discontinuation. The cycle of administration and discontinuation of administration of the CDK 4/6 inhibitor is repeated for at least two cycles. In further embodiments, the CDK 4/6 is selected from palbociclib, ribociclib, abemaciclib, trilaciclib, dalpiciclib, riviciclib, and combinations thereof. Preferably, the CDK 4/6 inhibitors is palbociclib. Furthermore, the palbociclib may be administered at a dose of 125 mg per day.

In some embodiments, the method includes co-administering an estrogen receptor antagonist to the human subject. Preferably, the estrogen receptor antagonist is fulvestrant. The fulvestrant may be administered at a dose of 500 mg every two weeks. Additionally, the fulvestrant may be administered at a dose of 500 mg every four weeks. In some instances, the fulvestrant is first administered at a dose of 500 mg every two weeks, which is then decreased to a dose of 500 mg every four weeks.

A further aspect of the present invention relates to a method of treating cancer in a human subject including selecting a human subject in need of treatment of cancer; administering to the human subject a therapeutically effective amount of gedatolisib, or a pharmaceutically acceptable salt, solvate, or ester thereof, and a CDK 4/6 inhibitor at least once a week for a period of three weeks; discontinuing administration of gedatolisib, or pharmaceutically acceptable salt, solvate, or ester thereof, and the CDK 4/6 inhibitor for a period of one week; and resuming administration of gedatolisib, or pharmaceutically acceptable salt, solvate, or ester thereof, and the CDK 4/6 inhibitor at least once a week following the period of discontinuation. The administration for at least a period of three weeks and discontinued administration for at least a period of one week constitutes a cycle, and this cycle is repeated for at least two cycles.

In some embodiments, the resumed administration of gedatolisib, or pharmaceutically acceptable salt, solvate, or ester thereof, and the CDK 4/6 inhibitor, occurs at least once a week for a period of three weeks.

Another aspect of the present invention relates to a method of treating cancer in a human subject including selecting a human subject in need of treatment of cancer; administering to the human subject a therapeutically effective amount of gedatolisib, or a pharmaceutically acceptable salt, solvate, or ester thereof, and a CDK 4/6 inhibitor at least once a week for a period of three weeks; discontinuing administration of gedatolisib, or pharmaceutically acceptable salt, solvate, or ester thereof, and the CDK 4/6 inhibitor for a period of one week; resuming administration of gedatolisib, or a pharmaceutically acceptable salt, solvate, or ester thereof, and the CDK 4/6 inhibitor at least once a week following the period of discontinuation, where the administration for at least a period of three weeks and discontinued administration for at least a period of one week constitutes a cycle, wherein the cycle is repeated for at least two cycles; and administering to the human subject an estrogen receptor antagonist.

In some embodiments, the subject's cancer is a solid cancer. Exemplary solid cancers include, but are not limited to, breast cancer, vaginal cancer, vulvar cancer, cervical cancer, uterine cancer, ovarian cancer, endometrial cancer, cancer of the Fallopian tubes, prostate cancer, testicular cancer, penile cancer, lung cancer, colorectal cancer, melanomas, bladder cancer, brain/CNS cancer, esophageal cancer, gastric cancer, head/neck cancer, kidney cancer, liver cancer, pancreatic cancer, and sarcomas.

In some embodiments, the subject's solid cancer is a hormone-dependent cancer. Exemplary hormone-dependent cancers include, but are not limited to, breast cancer, vaginal cancer, vulvar cancer, cervical cancer, uterine cancer, ovarian cancer, endometrial cancer, cancer of the Fallopian tubes, prostate cancer, testicular cancer, and penile cancer. In some embodiments, the hormone-dependent cancer is breast cancer. In further embodiments, the subject's breast cancer is metastatic, hormone resistant, estrogen receptor positive, estrogen receptor negative, progesterone receptor negative, progesterone receptor positive, triple negative, HER2 positive, or HER2 negative breast cancer. The breast cancer may also be either Basal or Luminal subtype. In further embodiments, the human subject is a pre-menopausal or post-menopausal female patient.

In some embodiments, the human subject has failed a prior treatment for cancer in a period of less than twelve months (e.g., in a period of less than six months). In some embodiments, the human subject has failed two or more prior treatments for cancer. The failed prior treatments may be endocrine or non-endocrine treatments for cancer. In one embodiment, the human subject has failed at least one endocrine treatment for cancer. In one embodiment, the human subject has failed at least one non-endocrine treatment for cancer.

DETAILED DESCRIPTION

Disclosed herein is a method of treating cancer (e.g., breast cancer) in a human patient. The method includes administering to the patient a therapeutically effective amount of gedatolisib, or a pharmaceutically acceptable salt, solvate, or ester thereof, at least once a week for a period of three weeks, followed by a period of one week with no administration of gedatolisib, or pharmaceutically acceptable salt, solvate, or ester thereof. This method constitutes a 28-day cycle (three doses administered weekly with gedatolisib, one week without gedatolisib), which is repeated for at least two cycles. The treatment of cancer patients using this cyclic admiration method has surprisingly been found to be more successful than the use of gedatolisib in a non-cyclic dosing regimen.

In order that the present description may be more readily understood, certain terms are first defined. Additional definitions are set forth throughout the detailed description. Unless defined otherwise, all technical and scientific terms used herein have the same meaning as commonly understood by one of ordinary skill in the art.

As used herein, the singular forms "a", "an" and "the" include plural referents unless the context clearly dictates otherwise. The use of "or" or "and" means "and/or" unless stated otherwise.

The term "about" as used herein when referring to a measurable value such as an amount, a temporal duration and the like, is encompasses variations of up to +10% from the specified value. Unless otherwise indicated, all numbers expressing quantities of ingredients, properties such as molecular weight, reaction conditions, etc., used herein are to be understood as being modified by the term "about".

Gedatolisib is a small molecule showing promise in the treatment of cancer, which inhibits Phosphatidylinositol-3 kinase and Mammalian Target of Rapamycin. Phosphatidylinositol-3 kinase (PI3K) is an enzyme that phosphorylates the 3-position of the inositol ring of phosphatidylinositol (D. Whitman et al., (1988)). Pluralities of PI3K subtypes exist, with three major subtypes of PI3Ks having now been identified based on their in vitro substrate specificity. These three are designated class I (a & b), class II, and class III (B. Vanhaesebroeck, (1997)).

The phosphoinositide 3-kinases signaling pathway is one of the most highly mutated systems in human cancers. PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110a, p110ß, p110δ, and p110γ) are typically activated by tyrosine kinases or G-protein coupled receptors to generate phosphatidylinositol (3,4,5)-trisphosphate (PIP3), which engages downstream effectors such as those in the AKT/PDK1 pathway, mTOR, the Tec family kinases, and the Rho family GTPases. The class II and III PI3Ks play a key role in intracellular trafficking through the synthesis of phosphatidylinositol 3-bisphosphate (PI(3)P) and phosphatidylinositol (3,4)-bisphosphate (PI(3,4)P2). The PI3Ks are protein kinases that control cell growth (mTORC1) or monitor genomic integrity (ATM, ATR, DNA-PK, and hSmg-1).

There are four mammalian isoforms of class I PI3Ks: PI3K-α, β, δ (class Ia PI3Ks) and PI3K-γ (a class Ib PI3K). These enzymes catalyze the production of PIP3, leading to activation of downstream effector pathways important for cellular survival, differentiation, and function. PI3K-α and PI3K-β are widely expressed and are important mediators of signaling from cell surface receptors. PI3K-α is the isoform most often found mutated in cancers and has a role in insulin signaling and glucose homeostasis (Knight et al., (2006); Vanhaesebroeck et al., (2010)). PI3K-β is activated in cancers where phosphatase and tensin homolog (PTEN) is deleted. Both isoforms are targets of small molecule therapeutics in development for cancer.

PI3K-δ and -γ are preferentially expressed in leukocytes and are important in leukocyte function. These isoforms also contribute to the development and maintenance of hematologic malignancies (Vanhaesebroeck et al., (2010); Clayton et al., (2002); Fung-Leung, (2011); Okkenhaug et al., (2002)). PI3K-δ is activated by cellular receptors (e.g., receptor tyrosine kinases) through interaction with the Sarc homology 2 (SH2) domains of the PI3K regulatory subunit (p85), or through direct interaction with RAS.

Selectivity versus other related kinases is also an important consideration for the development of PI3K inhibitors. While selective inhibitors may be preferred in order to avoid unwanted side effects, there have been reports that inhibition of multiple targets in the PI3K/Akt pathway (e.g., PI3Kα and mTOR [mammalian target of rapamycin]) may lead to greater efficacy.

Mammalian Target of Rapamycin (mTOR) is a cell-signaling protein that regulates the response of tumor cells to nutrients and growth factors, as well as controlling tumor blood supply through effects on Vascular Endothelial Growth Factor, VEGF. Inhibitors of mTOR starve cancer cells and shrink tumors by inhibiting the effect of mTOR. All mTOR inhibitors bind to the mTOR kinase. This has at least two important effects. First, mTOR is a downstream mediator of the PI3K/Akt pathway. The PI3K/Akt pathway is thought to be over activated in numerous cancers and may account for the widespread response from various cancers to mTOR inhibitors. The over-activation of the upstream pathway would normally cause mTOR kinase to be over activated as well. However, in the presence of mTOR inhibitors, this process is blocked. The blocking effect prevents mTOR from signaling to downstream pathways that control cell growth. Over-activation of the PI3K/Akt kinase pathway is frequently associated with mutations in the PTEN gene, which is common in many cancers and may help predict what tumors will respond to mTOR inhibitors. The second major effect of mTOR inhibition is anti-angiogenesis, via the lowering of VEGF levels.

As used herein the terms "gedatolisib" and "1-(4-{[4-(Dimethylamino)piperidin-1-yl]carbonyl}phenyl)-3-[4-(4, 6-dimorpholin-4-yl-1,3,5-triazin-2-yl)phenyl]urea" refer to the same compound and may be used interchangeably. In some embodiment of the present invention pharmaceutically acceptable salts, solvates or esters of gedatolisib, as would be known to those of skill in the art, may be used in the methods of treating cancer.

Representative "pharmaceutically acceptable salts" include but are not limited to, e.g., water-soluble and water-insoluble salts, such as the acetate, aluminum, amsonate (4,4-diaminostilbene-2,2-disulfonate), benzathine (N,N'-dibenzylethylenediamine), benzenesulfonate, benzoate, bicarbonate, bismuth, bisulfate, bitartrate, borate, bromide, butyrate, calcium, calcium edetate, camsylate (camphorsulfonate), carbonate, chloride, choline, citrate, clavulariate, diethanolamine, dihydrochloride, diphosphate, edetate, edisylate (camphorsulfonate), esylate (ethanesulfonate), ethylenediamine, fumarate, gluceptate (glucoheptonate), gluconate, glucuronate, glutamate, hexafluorophosphate, hexylresorcinate, hydrabamine(N,N'-bis(dehydroabietyl) ethylenediamine), hydrobromide, hydrochloride, hydroxynaphthoate, 1-hydroxy-2-naphthoate, 3-hydroxy-2-naphthoate, iodide, isothionate (2-hydroxyethanesulfonate), lactate, lactobionate, laurate, lauryl sulfate, lithium, magnesium, malate, maleate, mandelate, meglumine (1-deoxy-1-(methylamino)-D-glucitol), mesylate, methyl bromide, methylnitrate, methylsulfate, mucate, napsylate, nitrate, N-methylglucamine ammonium salt, oleate, oxalate, palmitate, pamoate (4,4'-methylenebis-3-hydroxy-2-naphthoate, or embonate), pantothenate, phosphate, picrate, polygalacturonate, potassium, propionate, p-toluenesulfonate, salicylate, sodium, stearate, subacetate, succinate, sulfate, sulfosaliculate, suramate, tannate, tartrate, teoclate (8-chloro-3,7-dihydro-1,3-dimethyl-1H-purine-2,6-dione), trieth iodide, tromethamine(2-amino-2-(hydroxymethyl)-1,3-propanediol), valerate, and zinc salts.

Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids.

Pharmaceutical acceptable solvates and hydrates are complexes of a compound with one or more solvent or water molecules, or 1 to about 100, or 1 to about 10, or one to about 2, 3 or 4, solvent or water molecules.

The term "inhibition" or "reduction" as used herein, refers to any statistically significant decrease in biological activity, including partial and full blocking of the activity. For example, "inhibition" or "reduction" can refer to a statistically significant decrease of about 10%, 20%, 30%, 40%, 50%, 60%, 70%, 80%, 90%, 95%, 96%, 97%, 98%, 99%, or 100% in biological activity. The terms "inhibits" or "blocks" (e.g., referring to inhibition/blocking of binding or activity) are used interchangeably and encompass both partial and complete inhibition/blocking.

As used herein, the term "subject" includes any human or non-human animal. For example, the methods and compositions described herein can be used to treat a subject (e.g., a human patient) having cancer. Preferably, the subjects are humans who have breast cancer and have experienced progression of their cancer during their prior treatment (e.g., an endocrine treatment) in a period of less than 12 months (e.g., in a period of less than 6 months).

A "therapeutically effective amount" means an amount of gedatolisib, or other active agent, set forth herein that, when administered to a subject, is effective in producing a therapeutic effect.

As used herein, "administering" refers to the physical introduction of a composition comprising a therapeutic agent to a subject, using any of the various methods and delivery systems known to those skilled in the art. Preferred routes of administration for the therapeutic agents described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intra-arterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually, or topically. Administering can also be performed, for example, once, a plurality of times, and/or over one or more extended periods.

As used herein, the terms "treatment," "treating", "treat", or the like, mean to alleviate or reduce the severity of at least one symptom or indication, to eliminate the causation of symptoms either on a temporary or permanent basis, or to obtain beneficial or desired clinical results. Beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may result in a partial response (PR) or a complete response (CR).

The term "endocrine treatment" or "hormonal treatment" (sometimes also referred to as "anti-hormonal treatment") denotes a treatment which targets hormone signaling, e.g. hormone inhibition, hormone receptor inhibition, use of hormone receptor agonists or antagonists, use of scavenger- or orphan receptors, use of hormone derivatives and interference with hormone production. Particular examples are tamoxifen therapy which modulates signaling of the estrogen receptor, or aromatase treatment which interferes with steroid hormone production.

The term "failed prior treatment" denotes that a subject who has been undergoing treatment for cancer has experienced a progression of the cancer during the treatment, e.g., within a specified time period of treatment (such as within twelve months, or six months of the onset of treatment). The term "progression" of a cancer denotes increased growth and/or spread (e.g., metastasis), typically measured by means established in the art for assessing cancer growth and/or spread, including but not limited to bodily scans (e.g., MRI scans, PET scans, CAT scans and the like), biopsies and/or measurement of biomarkers. In some embodiments, progression is defined as at least 20% increase in the sum of the diameters of the target measurable lesions (e.g., tumors) above the smallest sum observed, or over the baseline sum of diameters, with a minimum absolute increase of at least 5 mm.

The term "therapy modality", "therapy mode", "schedule", "regimen" as well as "therapy regimen" refers to a timely sequential or simultaneous administration of anti-tumor, and/or anti vascular, and/or immune stimulating, and/or blood cell proliferative agents, and/or radiation therapy, and/or hyperthermia, and/or hypothermia for cancer therapy. The administration of these can be performed in an adjuvant and/or neoadjuvant mode. The composition of such "protocol" may vary in the dose of the single agent, timeframe of application and frequency of administration within a defined therapy window.

The term "cytotoxic chemotherapy" refers to various treatment modalities affecting cell proliferation and/or survival. The treatment may include administration of alkylating agents, antimetabolites, anthracyclines, plant alkaloids, topoisomerase inhibitors, and other antitumor agents, including monoclonal antibodies and kinase inhibitors. In particular, the cytotoxic treatment may relate to a taxane treatment. Taxanes are plant alkaloids which block cell division by preventing microtubule function. The prototype taxane is the natural product paclitaxel, originally known as Taxol and first derived from the bark of the Pacific Yew tree. Docetazel is a semi-synthetic analogue of paclitaxel. Taxanes enhance stability of microtubules, preventing the separation of chromosomes during anaphase.

Various aspects described herein are described in further detail in the following subsections.

I. Gedatolisib

Provided herein are methods for treating cancer by administering to a subject (e.g., a human subject who has failed their prior treatment for cancer (e.g., an endocrine treatment for cancer) in less than a twelve-month period of time (e.g., a six-month period of time)) a therapeutically effective amount of gedatolisib, or a pharmaceutically acceptable salt, solvate, or ester thereof, in a cyclic manner. The cyclic administration, for example, can include administering gedatolisib to the subject for three weeks, followed by a period of discontinued administration for one week. This cycle may be repeated as many times as necessary to obtain the desired results.

Gedatolisib is a pan-class I isoform PI3K/mTOR inhibitor with high potency (NCT02626507, Apr. 24, 2020). The chemical synthesis of gedatolisib is disclosed in U.S. Pat. Nos. 8,039,469; 8,217,036; 8,445,486; 8,575,159; 8,748, 421; 8,859,542; 9,174,963; 10,022,381, which are hereby incorporated by reference in their entirety. Gedatolisib may be prepared in crystalline form and is chemically and physically stable at 25° C. and 60% Relative Humidity (RH) for up to 3 years in this form. However, this free base is insufficiently water soluble to allow the preparation of an aqueous solution formulation suitable for intravenous or parenteral administration at the therapeutic dosage levels required. Accordingly, formulations that allow for therapeutic dosage levels have been developed.

Pharmaceutical formulations comprising therapeutic dosage levels of gedatolisib are known in the art and include aqueous intravenous formulations, as well as nanoparticle formulations.

PCT application publication WO2016097949 discloses aqueous intravenous formulations of gedatolisib with lactic acid and/or orthophosphoric acid, which form clear, particulate free solutions. The formulations include gedatolisib, lactic acid, and water. The gedatolisib has a concentration in the solution less than 6 mg/ml (preferably about 5 mg/ml), and there is sufficient lactic acid present to provide a clear solution (preferably at least 2.5 mole equivalents). The gedatolisib forms a 1:1 (mole equivalent) lactate salt with lactic acid. Therefore, the formulations can be prepared using the gedatolisib free base or using a lactic acid salt of gedatolisib.

The formulations with orthophosphoric acid include gedatolisib, orthophosphoric acid, and water. The gedatolisib is present at a solution concentration of less than 4 mg/ml (preferably from 3.0 to 3.5 mg/ml) and sufficient orthophosphoric acid is present to provide a clear solution (preferably at least 5 mole equivalents).

Formulations including gedatolisib and cyclodextrins are disclosed in PCT Application Publication WO 2019234632. The pharmaceutical aqueous formulations include gedatolisib, or a pharmaceutically acceptable organic or inorganic acid salt thereof, a pharmaceutically acceptable organic or inorganic acid, which is not a sulphonic acid, a pharmaceutically acceptable beta- or gamma-cyclodextrin and water. The gedatolisib is present at a solution concentration of at least 6 mg/ml and the solutions are clear.

The pharmaceutically acceptable organic acid used (including for a salt thereof) are lactic acid, tartaric acid, malic acid, citric acid, succinic acid, acetic acid or maleic acid. The acid may be used in its racemic form, or as a single stereoisomeric form (or mixtures thereof), where applicable. Examples of a pharmaceutically acceptable beta-cyclodextrin are 2-hydroxypropyl-beta-cyclodextrin and sulphobutylether-β-cyclodextrin (SBECD). Examples of such a pharmaceutically acceptable gamma-cyclodextrin are gamma-cyclodextrin and 2-hydroxypropyl-gamma-cyclodextrin. The preferred amount of pharmaceutically acceptable beta- or gamma-cyclodextrin for use in the formulations is from 2 to 30% w/v, from 5 to 20% w/v, or from 15 to 30% w/v, and preferably is about 20% w/v or about 25% w/v. Preferably, the amount of pharmaceutically acceptable beta- or gamma-cyclodextrin for use in a formulation of the invention is about 20% w/v.

Formulations including gedatolisib and methanesulphonic acid and/or ethanesulphonic acid are disclosed in PCT application publication WO2019038657.

The formulations include gedatolisib, or a methanesulphonate salt thereof, methanesulphonic acid, and water. The gedatolisib is present at a solution concentration of less than 35 mg/ml or up to 30 mg/ml (preferably from 6 to 30 mg/ml) and sufficient methanesulphonic acid is present to provide a clear solution. Another formulation disclosed is gedatolisib, or an ethanesulphonate salt thereof, ethanesulphonic acid and water. The gedatolisib is present at a solution concentration of less than 35 mg/ml or up to 30 mg/ml (preferably from 6 to 30 mg/ml) and sufficient ethanesulphonic acid is present to provide a clear solution.

The use of methanesulphonic acid and ethanesulphonic acid enables a solution concentration of up to 30 mg/ml of gedatolisib to be achieved for a pharmaceutical aqueous solution formulation that is suitable for intravenous or parenteral administration to a patient, i.e. a clear, essentially particle-free solution.

In the above aqueous formulations, a solution concentration of gedatolisib that is at least 6 mg/ml is desirable to allow dose administration to subjects using a single vial presentation of the commercial drug product. A lyophilized drug product (for reconstitution) containing less than 6 mg/ml drug product solution will require multiple vials to deliver the required therapeutic dose. A multiple vial approach to dose delivery is not desirable given current regulatory expectations for these product types.

Any of the above-mentioned formulations may be freeze-dried to provide a lyophilized solid composition, a bulking agent may be added to the formulation prior to the freeze-drying process commencing. A bulking agent may not be present if the formulation of the invention contains a pharmaceutically acceptable beta- or gamma-cyclodextrin. The primary function of the bulking agent is to provide the freeze-dried solid with a non-collapsible, structural integrity that will allow rapid reconstitution on constitution of the aqueous formulation prior to administration, and it should also facilitate efficient lyophilization. Bulking agents are typically used when the total mass of solutes in the formulation is less than 2 g/100 ml. Bulking agents may also be added to achieve isotonicity with blood. The bulking agent may be selected from a saccharide, sugar alcohol, amino acid or polymer, or be a mixture of two or more of any thereof. Preferably, the bulking agent is a sugar or sugar alcohol, or a mixture thereof. Preferably, the sugar is sucrose. Preferably, the sugar alcohol is mannitol. Constitution of the lyophilized solid composition may be achieved using an appropriate quantity of water and/or an aqueous solution of a suitable tonicity modifier in order to ensure that a clear solution is obtained.

Therapeutic agents containing at least one basic nitrogen atom (i.e., protonatable nitrogen-containing therapeutic agents), such as gedatolisib, represent an important group of therapeutic agents. However, nanoparticle formulations of this class of drugs are often hindered by undesirable properties, e.g., unfavorable burst release profiles and poor drug loading. PCT application publication WO2015138835 discloses therapeutic nanoparticles of gedatolisib which have a controlled release rate of the therapeutic agent.

The therapeutic nanoparticles include gedatolisib (preferably in an amount of about 1 to 20 weight percent), a substantially hydrophobic acid, and a polymer selected from diblock poly(lactic) acid-poly(ethylene)glycol copolymer or a diblock poly(lactic acid-co-glycolic acid)-poly(ethylene) glycol copolymer, and combination thereof. The molar ratio of the substantially hydrophobic acid to the gedatolisib ranges from about 0.25:1 to about 2:1 and the $pK_a$ of the protonated gedatolisib is at least about 1.0 $pK_a$ units greater than the $pK_a$ of the hydrophobic acid. The hydrophobic acid and the gedatolisib form a hydrophobic ion pair in the therapeutic nanoparticle. Additionally, the nanoparticles can include a targeting ligand, which may increase target binding (cell binding/target uptake), making the nanoparticle target specific.

In general, a "nanoparticle" refers to any particle having a diameter of less than 1000 nm. Preferably, the therapeutic nanoparticles may have a diameter ranging from 60 to 120 nm. For example, the nanoparticle may have a diameter ranging from about 60 nm, about 70 nm, about 80 nm, about 90 nm, about 100 nm, or about 110 nm, up to about 70 nm, about 80 nm, about 90 nm, about 100 nm, about 110 nm, or about 120 nm.

As used herein, the "substantially hydrophobic acid" is an acid which has a $pK_a$ in water of about −1.0 to about 5.0. Preferably, the substantially hydrophobic acid has a $pK_a$ in water of about 2.0 to about 5.0. Exemplary substantially hydrophobic acids include, but are not limited to, fatty acids. For example, the fatty acid may be a saturated fatty acid, including, but not limited to, caproic acid, enanthic acid, caprylic acid, pelargonic acid, capric acid, undecanoic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, or combinations thereof. Additionally, the fatty acid may be a omega-3 fatty acid, including, but not limited to, hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, or combinations thereof. The fatty acid may also be an omega-6 fatty acid, including, but not limited to, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, or combinations thereof. The fatty acid may also be an omega-9 fatty acid, including, but not limited to, oleic acid, eicosenoic acid, mead acid, erucic acid, nervonic acid, or combinations thereof. The fatty acid may also be a polyunsaturated fatty acid, including, but not limited, rumenic acid, a-calendic acid, β-calendic acid, jacaric acid, a-eleostearic acid, β-eleostearic acid, catalpic acid, punicic acid, rumelenic acid, a-parinaric acid, β-parinaric acid, bosseopentaenoic acid, pinolenic acid, podocarpic acid, or combinations thereof.

Alternatively, the hydrophobic acid can be a bile acid. For example, in some embodiments, the bile acid includes but is not limited to, chenodeoxycholic acid, ursodeoxycholic acid, deoxycholic acid, hycholic acid, beta-muricholic acid, cholic acid, lithocholic acid, an amino acid-conjugated bile acid, or combinations thereof.

Alternatively, the hydrophobic acid may include but is not limited to, dioctyl sulfosuccinic acid, 1-hydroxy-2-naphthoic acid, dodecylsulfuric acid, naphthalene-1,5-disulfonic acid, naphthalene-2-sulfonic acid, pamoic acid, undecanoic acid, or combinations thereof.

The nanoparticles may be combined with pharmaceutically acceptable carriers to form a pharmaceutical composition. As would be appreciated by one of skill in this art, the carriers may be chosen based on the route of administration, the location of the target issue, the time course of delivery of the drug, etc.

The pharmaceutical nanoparticle compositions can be administered to a patient or subject by any means known in the art including oral and parenteral routes. The nanoparticle compositions may be administered by injection (e.g., intravenous, subcutaneous or intramuscular, intraperitoneal injection), rectally, vaginally, topically (as by powders, creams, ointments, or drops), or by inhalation (as by sprays).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) Tween™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing the gedatolisib is chosen by the individual physician in view of the patient to be treated, in general, dosage and administration are adjusted to provide an effective amount of the gedatolisib nanoparticle to the patient being treated. As used herein, the "effective amount" of the nanoparticles containing gedatolisib refers to the amount necessary to elicit the desired biological response. As will be appreciated by those of ordinary skill in this art, the effective amount of a nanoparticle containing the gedatolisib may vary depending on such factors as the desired biological endpoint, the target tissue, the route of administration, etc. For example, the effective amount of the nanoparticle might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

Aqueous pharmaceutical formulations of gedatolisib, such as those described above, that are suitable for intravenous administration generally have a pH of from 3 to 9. However, lower pH values are tolerated in certain settings. The pH may range from about 3, 3.5, 4, 4.5, 5, 5.5, 6, 6.5, 7, 7.5, or 8 up to about 3.5, 4, 4.5, 5, 5.5, 6, 6.5, 7, 7.5, 8, 8.5, or 9. Preferably, the pH is from 3 to 8 or from 4 to 8.

The weekly dose of gedatolisib to be administered by the intravenous route for the treatment of cancer using the above-mentioned formulations is preferably in the range of from 100-400 mg/ml per week. For example, the dose may be about 100 mg/ml per week, about 110 mg/ml per week, about 120 mg/ml per week, about 130 mg/ml per week, about 140 mg/ml per week, about 150 mg/ml per week, about 160 mg/ml per week, about 170 mg/ml per week, about 180 mg/ml per week, about 190 mg/ml per week, 200 mg/ml per week, about 210 mg/ml per week, about 220 mg/ml per week, about 230 mg/ml per week, about 240 mg/ml per week, about 250 mg/ml per week, about 260 mg/ml per week, about 270 mg/ml per week, about 280 mg/ml per week, about 290 mg/ml per week, 300 mg/ml per week, about 310 mg/ml per week, about 320 mg/ml per week, about 330 mg/ml per week, about 340 mg/ml per week, about 350 mg/ml per week, about 360 mg/ml per week, about 370 mg/ml per week, about 380 mg/ml per week, about 390 mg/ml per week, or 400 mg/ml per week.

II. CDK 4/6 Inhibitors

In some embodiments of the present application, the method of treating cancer includes co-administering to the subject a CDK 4/6 inhibitor along with gedatolisib. As used herein, the term "CDK 4/6 inhibitor" includes compounds that inhibit CDK4 activity, CDK6 activity, or both CDK4 and CDK6 activity.

The regulation of the cell cycle is governed and controlled by specific proteins, which are activated and deactivated mainly through phosphorylation/dephosphorylation processes in a precisely timed manner. The key proteins that coordinate the initiation, progression, and completion of cell-cycle program are cyclin dependent kinases (CDKs). Cyclin-dependent kinases belong to the serine-threonine protein kinase family. They are heterodimeric complexes composed of a catalytic kinase subunit and a regulatory cyclin subunit. CDK activity is controlled by association with their corresponding regulatory subunits (cyclins) and CDK inhibitor proteins (Cip & Kip proteins, INK4s), by their phosphorylation state, and by ubiquitin-mediated proteolytic degradation.

There are four CDKs that are significantly involved in cellular proliferation: CDK1, which predominantly regulates the transition from G2 to M phase, and CDK2, CDK4, and CDK6, which regulate the transition from G1 to S phase. In early to mid G1 phase, when the cell is responsive to mitogenic stimuli, activation of CDK4-cyclin D and CDK6-cyclin D induces phosphorylation of the retinoblastoma protein (pRb). Phosphorylation of pRb releases the transcription factor E2F, which enters the nucleus to activate transcription of other cyclins which promote further progression of the cell cycle. CDK4 and CDK6 are closely related proteins with basically indistinguishable biochemical properties.

A number of CDK 4/6 inhibitors have been identified, including specific pyrido[2,3-d]pyrimidines, 2-anilinopyrimidines, diaryl ureas, benzoyl-2,4-diaminothiazoles, indolo[6,7-a]pyrrolo[3,4-c]carbazoles, and oxindoles. For example, WO 03/062236 identifies a series of 2-(pyridin-2-ylamino-pyrido[2,3]pyrimidin-7-ones for the treatment of Rb positive cancers that show selectivity for CDK4/6, including 6-acetyl-8-cyclopentyl-5-methyl-2-(5-piperazin-1-yl-pyridin-2-ylammino)-8H-pyrido-[2,3-d]-pyrimidin-7-one (PD0332991). Tate, et al. describe the antitumor activity of the CDK4/6 inhibitor abemaciclib (LY2835219) ("Semi-Mechanistic Pharmacokinetic/Pharmacodynamic Modeling of the Antitumor Activity of LY2835219, a New Cyclin-Dependent Kinase 4/6 Inhibitor, in Mice Bearing Human Tumor Xenografts", Clin Cancer Res (Jul. 15, 2014) 20; 3763). Rader, et al. describe the reduced proliferation in neuroblastoma-derived cell lines using the CDK4/6 inhibitor ribociclib (LEE011) ("Dual CDK4/CDK6 Inhibition Induces Cell Cycle Arrest and Senescence in Neuroblastoma", Clin Cancer Res (Nov. 15, 2013) 19(22): 6173-82). VanderWel et al. describe an iodine-containing pyrido[2,3-d]pyrimidine-7-one (CKIA) as a potent and selective CDK4 inhibitor (see VanderWel et al., J. Med. Chem. 48 (2005) 2371-2387). WO 99/15500 filed by Glaxo Group Ltd discloses protein kinase and serine/threonine kinase inhibitors. WO 2010/020675 filed by Novartis AG describes pyrrolopyrimidine compounds as CDK inhibitors. WO 2011/101409 also filed by Novartis describes pyrrolopyrimidines with CDK 4/6 inhibitory activity. WO 2005/052147 filed by Novartis and WO 2006/074985 filed by Janssen Pharma disclose additional CDK4 inhibitors. WO 2012/061156 filed by Tavares and assigned to G1 Therapeutics describes CDK inhibitors. WO 2013/148748 filed by Francis Tavares and assigned to G1 Therapeutics describes Lactam Kinase Inhibitors.

Selective CDK4/6 inhibitors are generally designed to target CDK4/6-replication dependent cancers. For example, Michaud et al., reported that the CDK4/6 inhibitor PD-0332991 was inactive against Rb-negative tumors. (Michaud et al., Pharmacologic Inhibition of Cyclin-Dependent Kinase 4 and 6 Arrests the Growth of Glioblastoma Multiform Intracranial Xenografts. Cancer Res. 70:3228-3238 (2010)).

In some embodiments, the CDK 4/6 inhibitor is selected from the group consisting of palbociclib, ribociclib, abemaciclib, trilaciclib, dalpiciclib, riviciclib, and combinations thereof.

The CDK 4/6 inhibitor may be administered using the methods as known in the art. In some embodiment, the CDK 4/6 inhibitor is palbociclib. Palbociclib (Ibrance™, Pfizer, New York, NY) is available in 125 mg, 100 mg, and 75 mg tablets and capsules. See Ibrance™ Prescribing Information. The recommended dose of palbociclib is 125 mg taken orally once daily for 21 consecutive days followed by 7 days off treatment to comprise a complete cycle of 28 days. Id. This treatment cycle may be modified based on the results of treatment and the tolerance of the patient. Id. For example, if patients experience neutropenia the administration of the palbociclib can be reduced to 100 mg, or 75 mg once daily for 21 consecutive days followed by 7 days off treatment. Id.

Ribociclib (Kisqali™, Novartis, Switzerland) is available in 200 mg tablets. See Kisqali™ Prescribing Information. The recommended dose of ribociclib is 600 mg (three 200 mg tables) taken orally once daily for 21 consecutive days followed by 7 days off treatment to comprise a complete cycle of 28 days. Id. This treatment cycle may be modified based on the results of treatment and the tolerance of the patient. Id. For example, if patients experience negative side effects administration of the ribociclib can be reduced to 400 mg, or 200 mg once daily for 21 consecutive days followed by 7 days off treatment. Id.

Abemaciclib (Verzenio™, Eli Lilly, Indianapolis, IN) is available in 200 mg, 150 mg, 100 mg, and 50 mg tablets. See Verzenio™ Prescribing Information. The recommended dose of abemaciclib when administered in combination with fulvestrant is 150 mg twice daily. Id. The recommended dose of abemaciclib when administered without fulvestrant is 200 mg twice daily. Id. If dose reduction is necessary, it is recommended to reduce the abemaciclib dose by 50 mg at a time. Id.

Trilaciclib (Cosela™, G1 Therapeutics, Inc., NC) is available in a 300 mg lyophilized powder in a single-dose vial. See Cosela™ Prescribing Information. The recommended dose of trilaciclib is 240 mg/m$^2$ per dose administered as an intravenous (IV) infusion. Id. The trilaciclib should be reconstituted with 19.5 mL of 0.9% Sodium Chloride Injection or 5% Dextrose Injection, USP, to obtain a concentration of 15 mg/mL. Id. Trilaciclib is generally administered as 30-minute intravenous infusion which must be completed within 4 hours prior to the start of chemotherapy on each day chemotherapy is administered. Id.

Dalpiciclib (SHR6390, Jiangsu Hengrui Medicine Co.) is in clinical trials and has been dosed 150 mg, orally once daily on Day 1 to Day 21 of every 28-day cycle, followed by 7 days off treatment. See NCT04236310, Jan. 17, 2020. Dalpiciclib is currently being investigated in in combination with letrozole or anastrozole or fulvestrant in patients with HR-positive and HER2-negative advanced breast cancer.

Riviciclib (P276-00, Piramal Enterprises Ltd., Mumbai, IN) is in clinical trials and has been administered as an intravenous infusion at a concentration of 185 mg/m$^2$ in 200 ml of 5% dextrose over 30 min per day from days 1 to 5 of a 21-day cycle. See NCT00898287, Jan. 20, 2012. Riviciclib has been investigated in in combination with gemcitabine and carboplatin in patients with metastatic triple negative breast cancer.

II. Estrogen Receptor Antagonists

The estrogen receptor (ER) is a ligand-activated transcriptional regulatory protein that mediates induction of a variety of biological effects through its interaction with endogenous estrogens. Endogenous estrogens include 17β (beta)-estradiol and estrones. ER has been found to have two isoforms, ER-α (alpha) and ER-β (beta).

In some embodiments of the present application, the method of treating cancer includes co-administering to the subject an estrogen receptor antagonist along with gedatolisib, and optionally a CDK4/6 inhibitor. As used herein, the term "estrogen receptor antagonist" includes compounds that act competitively by displacing estrogens from the receptor.

ARN-810 (GDC-0810, Seragon Pharmaceuticals, Genentech Inc.) is a small molecule, nonsteroidal, selective ER modulator that antagonizes the effects of estrogens and induces ER degradation via proteasome. ARN-810 is in clinical trials as an orally-delivered therapy to treat advanced metastatic ER-α positive (ER+) breast cancer.

PCT Application Publication WO2013/090836 discloses fluorinated estrogen receptor modulators and uses thereof.

PCT Application Publication WO2014/205136 discloses azetidine estrogen receptor modulators and uses thereof.

U.S. Patent Application Publication No. 2003/0130274 discloses 2-phenyl-1-[4-(2-aminoethoxy)benzyl]-indoles as estrogenic agents.

One exemplary estrogen receptor antagonist useful for the methods of the present application is fulvestrant.

Fulvestrant (Faslodex™, AstraZeneca, Cambridge, UK) is available an injection for intramuscular administration, supplied as a 250 mg/5 mL vial. See Faslodex™ Prescribing Information. The recommended dosing of fulvestrant is 500 mg intramuscularly into the buttocks (gluteal area) slowly as two 5 mL injections, on Days 1, 15, 29, and once monthly thereafter. See id. For patients with moderate hepatic impairment the recommended dose is 250 mg administered intramuscularly as one 5 mL injection on Days 1, 15, 29, and once monthly thereafter. See id.

IV. Formulations

In some embodiments, the gedatolisib, CDK 4/6 inhibitors, and estrogen receptor antagonists used in the method of the present application can be formulated with one or more pharmaceutically acceptable excipients to form pharmaceutical compositions.

The pharmaceutical compositions used in the methods disclosed herein may be specially formulated in solid or liquid form, including those adapted for parenteral administration, for example, by intravenous, subcutaneous, intratumoral or intramuscular injection or infusion as, for example, a sterile solution or suspension.

Injectable formulations or formulations for infusion of the pharmaceutical compositions used in the methods disclosed herein may be prepared by known methods. For example, the injectable or infusible formulation may be prepared, e.g., by dissolving, suspending or emulsifying an FcRn inhibitor or its salt in a sterile aqueous medium or an oily medium conventionally used for injections. As the aqueous medium for injections or infusions, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant (e.g., polysorbate 80, HCO-50 (polyoxyethylene (50 mol) adduct of hydrogenated castor oil)), etc. As the oily medium, there are employed, e.g., sesame oil, soybean oil, etc., which may be used in combination with a solubilizing agent such as benzyl benzoate, benzyl alcohol, etc. The injectable or infusible formulation thus prepared is preferably filled in an appropriate injection ampoule or in a vial or bag suitable for infusion.

A pharmaceutically acceptable excipient can be a pharmaceutically acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject, bulking agent, salt, surfactant and/or a preservative. Some examples of materials which can serve as pharmaceutically acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations.

A bulking agent is a compound that adds mass to a pharmaceutical formulation and contributes to the physical structure of the formulation in lyophilized form. Suitable bulking agents according to the present invention include mannitol, glycine, polyethylene glycol and sorbitol.

The use of a surfactant can reduce aggregation of a reconstituted protein and/or reduce the formation of particulates in the reconstituted formulation. The amount of surfactant added is such that it reduces aggregation of the reconstituted protein and minimizes the formation of particulates after reconstitution. Suitable surfactants according to the present invention include polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and polyethyl glycol, polypropyl glycol, and copolymers of ethylene and propylene glycol (e.g. Pluronics, PF68, etc.).

Preservatives may be used in formulations provided herein. Suitable preservatives for use in the formulation of the invention include octadecyldimethylbenzyl ammonium chloride, hexamethonium chloride, benzalkonium chloride (a mixture of alkylbenzyl-dimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

In some embodiments, the gedatolisib, and optionally the CDK 4/6 inhibitors, and/or estrogen receptor antagonists, used in the methods disclosed herein may be lyophilized and provided in a composition for reconstitution prior to administration.

V. Kits and Unit Dosage Forms

Also provided herein are kits that include a pharmaceutical composition containing gedatolisib, and optionally the CDK 4/6 inhibitors, and/or estrogen receptor antagonists, and pharmaceutically acceptable carrier, in a therapeutically effective amount adapted for use in the methods described herein. The kits optionally also can include instructions, e.g., comprising administration schedules, to allow a practitioner (e.g., a physician, nurse or patient) to administer the composition contained therein to a patient having cancer. The kit also can include a syringe.

Optionally, the kits include multiple packages of the single-dose pharmaceutical compositions each containing an effective amount of the gedatolisib for a single administration (e.g., 180 mg) in accordance with the methods provided above. Instruments or devices necessary for administering the pharmaceutical composition(s) also may be included in the kits. For instance, a kit may provide one or more pre-filled syringes containing an amount of the liquid necessary for reconstitution of the gedatolisib.

VI. Subject Population

The subjects treated with the methods described herein may have one or more of the characteristics below.

In one embodiment, subjects are in need of treatment of cancer. In some embodiments, the cancer is a solid cancer (i.e., a solid tumor). The solid cancer may be selected from the group consisting of breast cancer, vaginal cancer, vulvar cancer, cervical cancer, uterine cancer, ovarian cancer, endometrial cancer, cancer of the Fallopian tubes, prostate cancer, testicular cancer, penile cancer, lung cancer, colorectal cancer, melanomas, bladder cancer, brain/CNS cancer, esophageal cancer, gastric cancer, head/neck cancer, kidney cancer, liver cancer, pancreatic cancer, and sarcomas.

Cancers that can be treated with the methods and compositions described herein include, but are not limited to, solid cancers that are hormone-dependent, hormone responsive, and/or hormone sensitive (collectively "hormone responsive cancers"). Exemplary cancers that can be treated include, without limitation, androgen-responsive cancers, such as estrogen-responsive cancers, and testosterone-responsive cancers. In some embodiments, the cancer can be a non-hormone responsive cancer of a cancer that previously responded to hormone treatment but later became non-hormone unresponsive. Exemplary hormone-dependent cancers include, but are not limited to, breast cancer, vaginal cancer, vulvar cancer, cervical cancer, uterine cancer, ovarian cancer, endometrial cancer, cancer of the Fallopian tubes, prostate cancer, testicular cancer, and penile cancer. In some embodiments, the hormone-dependent cancer is breast cancer.

In some embodiments, the subjects of the methods herein are in need of treatment of breast cancer. The breast cancer may be diagnosed using any known methods in the art. For example, the cancer may be diagnosed through testing of the subject's tumor (e.g., a tumor biopsy), blood, bodily fluid, or other tissue. The subject may also undergo biomarker testing to determine the classification of the breast cancer.

The term "biomarker" refers, in the most general sense, to a biological metric of the condition of a cell or patient health or disease status. A non-limiting listing of general biomarkers includes biologically derived molecules found in a mammal, biological activity of a mammalian cell or tissue, gene copy number, gene mutations, single nucleotide polymorphisms, gene expression levels, mRNA levels, splice variants, transcriptional modifications, post-transcriptional modifications, epi-genetic modifications, cell surface markers, differential expression of a protein or nucleic acid (including all forms of functional RNA), amplification of a nucleic acid, cell morphology, post-translational modifications, protein truncations, phosphorylations, dephosphorylations, ubiquitination, de-ubiquitination, metabolites, hormones at any stage of biosynthesis, cytokines, chemokines, and combinations thereof. A subset of biomarkers are used for diagnostic and therapeutic selection purposes to help pathologists diagnose disease and to help doctors prescribe therapy. Biomarkers typically measure, in fixed, mounted tissue, a gene copy number, a genetic mutation, or the level of a protein without specification of the state or activity of the protein.

The term "biomarker status" refers to assessment of a biomarker(s) in a patient, or patient's cells, and typically is reported as "biomarker positive" when the biomarker is present or "biomarker negative" when the biomarker is absent. When a protein receptor is used as a biomarker (e.g. HER2/ErbB2 or ER), a biomarker positive result is also referred to as the receptor being over-expressed or amplified and a biomarker negative result is referred to as the receptor being normally expressed or non-amplified. For diseases where a biomarker or biomarker signature is a prognostic indicator of disease progression or predicts therapeutic efficacy, current clinical practice relies on the measurement of the amount of biomarker or its related mutations to refine a patient's diagnosis by classifying the patient as either biomarker negative or positive.

The term "HER2/ErbB2 status" refers to assessment of expression of HER2/ErbB2 in a patient, or patient's cells (e.g., cancer cells) as a biomarker, and the status typically is reported as "HER2/ErbB2 positive" when the biomarker is present in overabundance as compared to a normal healthy non-cancer breast tissue sample or "HER2/ErbB2 negative" when the biomarker is present at a level no greater than a normal healthy non-cancer breast tissue sample as determined by an IHC stain test of a fixed tissue sample. Various methods are known in the art for assessing HER2/ErbB2 status, typically focusing on the amount of the receptor (IHC), or mRNA levels (qPCR), or gene copy number (FISH), that is expressed by a patient's cells to thereby diagnose a patient as HER2/ErbB positive (when this receptor is overexpressed or amplified in the patient's cells) or HER2/ErbB negative (when this receptor is not overexpressed or not amplified on patient's cells). Overexpression and amplification are terms of art describing levels elevated above those found in similar tissue from a normal disease-free individual.

The terms "estrogen receptor status" or "ER status" refer to assessment of expression of ER in a patient, or patient's cells (e.g., cancer cells) as a biomarker, and the status typically is reported as "ER positive" when the biomarker is overexpressed in the nucleii of a stained fixed specimen or "ER negative" when the biomarker is normally expressed or absent in the nucleii of a stained fixed specimen. Various methods are known in the art for assessing ER status, typically focusing on the amount of the receptor (IHC), or mRNA levels (qPCR), that is expressed by a patient's cells to thereby diagnose a patient as ER positive (when this receptor is expressed the patient's cells) or ER negative (when this receptor is not expressed on patient's cells).

The term "targeted pathway drug," "pathway drug," or "targeted drug," refers to any molecule or antibody with therapeutic capacity designed to bind to a specific biomolecule (e.g. protein) involved in a disease process, thereby regulating its activity.

The terms "HER2 therapy" or "HER2-targeted therapy" refer to treatments using one or more therapeutic agents that are designed to specifically target the HER2 molecule and/or signaling pathway(s), including but not limited to, for example antibodies and small molecules that target the HER2 molecule and/or signaling pathway(s). Such HER2 therapies may also target other members of the HER family, for example therapies that target both HER1 and HER2, HER1, HER2, and HER4, or HER3 alone.

The terms "ER therapy", "ER-targeted therapy" or "hormonal therapy" refer to treatments using one or more therapeutic agents that are designed to specifically target the ER molecule and/or signaling pathway(s), including but not limited to aromatase inhibitors, selective estrogen receptor modulators and selective estrogen receptor degrader, as well as the combination of such therapies with therapies that inhibit cyclin-dependent kinases CDK4 and CDK6.

In some embodiments the breast cancer is metastatic, hormone resistant, estrogen receptor positive, estrogen receptor negative, progesterone receptor negative, progesterone receptor positive, triple negative, HER2 positive, or HER2 negative breast cancer. In further embodiments, the subject is a pre-menopausal or post-menopausal female patient.

In some embodiments the breast cancer is Basal or Luminal subtype. Breast cancer is known to be a heterogeneous disease. There are different subtypes that can be defined based on (i) a molecular profile of a breast cancer tumor, (ii) gene array testing, or (iii) an immunohistochemical analysis approach. In particular, mammary ducts are bi-layered structures composed of a luminal layer and a myoepithelial layer that adhere to a basement membrane. The term basal refers to certain cancers that arise from the basal layer of the stratified epithelia. Breast carcinomas of the basal subtype reside in the basal layer of the ductal epithelium of the breast as opposed to the apical or luminal layers. Such cancers have distinct cytological features and gene expression profiles such as an intermediate filament profile (cytokeratins) first observed in the basal cells of the skin.

Approximately 14-20% of breast cancers are basal-like. Basal-like breast cancers differ to luminal cancers in being triple negative for the immunophenotypic markers ER−/PR−/HER2− but express CK5/6. Basal-like breast cancers show increased hypoxia and high tumor grade and have an aggressive phenotype characterized by high cell proliferation and poor clinical outcome. Most BRCA1 breast cancers and many BRCA2 breast cancers are both triple negative/basal-like. Triple negative/basal-like tumors are often aggressive and have a poorer prognosis compared to the estrogen receptor-positive subtypes (luminal A and luminal B tumors). Triple negative/basal-like tumors are usually treated with some combination of surgery, radiation therapy and chemotherapy. These tumors cannot be treated with hormone therapies or trastuzumab because they are hormone receptor-negative and HER2/neu-negative.

Most breast cancers are luminal tumors. Luminal tumor cells look like the cells of breast cancers that start in the inner (luminal) cells lining the mammary ducts. Luminal A breast cancers are ER+ and/or PR+, HER2−, low Ki67. About 42-59% of breast cancers are luminal A. Luminal A tumors tend to be of low or moderate tumor grade. Of the four subtypes, luminal A tumors tend to have the best prognosis, with fairly high survival rates and fairly low recurrence rates. Only about 15% of luminal A tumors have p53 mutations, a factor linked with a poorer prognosis.

Luminal B breast cancers are ER+ and/or PR+, HER2+ (or HER2− with high Ki67). About 6-17% of breast cancers are luminal B. Women with luminal B tumors are often diagnosed at a younger age than those with luminal A tumors. Compared to luminal A tumors, luminal B tumors also tend to have factors that lead to a poorer prognosis including: poorer tumor grade; larger tumor size; and p53 gene mutations. In general, women with luminal B tumors have fairly high survival rates, although not as high as those with luminal A tumors.

In some embodiments, the breast cancer is ductal carcinoma in situ (intraductal carcinoma), lobular carcinoma in situ, invasive (or infiltrating) ductal carcinoma, invasive (or infiltrating) lobular carcinoma, inflammatory breast cancer, triple-negative breast cancer, paget disease of the nipple, phyllodes tumor, angiosarcoma or invasive breast carcinoma. In some embodiments, the invasive breast carcinoma is further categorized into subtypes. In some embodiments, the subtypes include adenoid cystic (or adenocystic) carcinoma, low-grade adenosquamous carcinoma, medullary carcinoma, mucinous (or colloid) carcinoma, papillary carcinoma, tubular carcinoma, metaplastic carcinoma, micropapillary carcinoma or mixed carcinoma.

In some embodiments, the breast cancer is classified according to stages or how far the tumor cells have spread within the breast tissues and to other portions of the body. There are five stages of breast cancer, Stage 0-IV. The method of treating cancer described herein may be used to treat patients with breast cancer classified as Stage 0-Stage IV.

Stage 0 breast cancer refers to non-invasive breast cancers or that there are no evidence of cancer cells or abnormal non-cancerous cells breaking out of the origin site. Stage I breast cancer refers to invasive breast cancer in which the cancer cells have invaded into surrounding tissues. Stage I is subclassified into Stage IA and IB, in which Stage IA describes tumor measures up to 2 cm with no spread of cancer cells. Stage IB describes absence of tumor in breast but have small lumps of cancer cells between 0.2 mm to 2 mm within the lymph nodes. Stage II breast cancer is further subdivided into Stage IIA and IIB. Stage IIA describes tumor between 2 cm to 5 cm in breast only, or absence of tumor in breast but with cancer between 2 mm to 2 cm in axillary lymph nodes. Stage IIB describes tumor larger than 5 cm in breast only, or tumor between 2 cm to 5 cm in breast with presence of small tumors from 0.2 mm to 2 mm in axillary lymph nodes. Stage III breast cancer is further subdivided into Stage IIIA, IIIB, and IIIC. Stage IIIA describes absence of tumor or tumor greater than 5 cm in breast with small tumors in 4-9 axillary lymph nodes or small tumors 0.2 mm-2 mm in size in axillary lymph nodes. Stage IIIB describes tumor spreading into the chest wall or skin of the breast causing swelling or ulcer and with presence of tumor in up to 9 axillary lymph nodes. Inflammatory breast cancer is also considered as Stage IIIB. Stage IIIC describes absence of tumor or tumor spreading into the chest wall or to the skin of the breast, with tumor present in 10 or more axillary lymph nodes. Stage IV breast cancer refers to invasive breast cancer that has metastasized into the lymph nodes and other portions of the body.

In other embodiments, the cancer may be adrenal cancer, cancer of the lymphatic system, such as the lymph nodes, leukemia, lymphoma, myeloma, Waldenstrom's macroglobulinemia, monoclonal gammopathy, benign monoclonal gammopathy, heavy chain disease, bone and connective tissue sarcoma, brain tumors, thyroid cancer, pancreatic cancer, pituitary cancer, eye cancer, esophageal cancer, stomach cancer, colon cancer, rectal cancer, liver cancer, gallbladder cancer, cholangiocarcinoma, lung cancer, oral cancer, skin cancer, kidney cancers, Wilms' tumor, and bladder cancer.

In some embodiments, the human subject has failed a prior treatment (e.g., an endocrine treatment) for cancer (e.g., breast cancer) in a period of less than twelve months (e.g., less than six months). In some embodiments, the human subject has failed two or more prior treatments for cancer. The failed prior treatment(s) may be a endocrine treatment(s) and/or a non-endocrine treatment(s) for cancer.

VII. Administration

The administration of gedatolisib in a 28-day cycle (administered weekly for three weeks, and one week without gedatolisib) was found to be more effective when compared to the non-cyclic (weekly) administration schedule. The 28-day cycle includes administered of gedatolisib intravenously once a week for three weeks (e.g., on days 1, 8, and 15 of the cycle), followed by a week without administration of gedatolisib (e.g., no administration of gedatolisib on day 21).

One aspect of the present invention relates to a method of treating cancer in a human subject. The method includes selecting a human subject in need of treatment of cancer. The human subject is administered a therapeutically effective amount of gedatolisib, or a pharmaceutically acceptable salt, solvate, or ester thereof, at least once a week for a period of three weeks. This is followed by a week in which the administration of gedatolisib, or pharmaceutically acceptable salt, solvate, or ester thereof, is discontinued. The administration of gedatolisib, or pharmaceutically acceptable salt, solvate, or ester thereof, is then resumed at least once a week following the period of discontinuation. The administration for at least a period of three weeks and discontinued administration for at least a period of one week constitutes a cycle, and the cycle is repeated for at least two cycles.

In some embodiments, the resumed administration of gedatolisib, or pharmaceutically acceptable salt, solvate, or ester thereof, occurs at least once a week for a period of three weeks.

In further embodiments, the cycle of administration occurs for at least 3 cycles, at least 4 cycles, at least 5 cycles, at least 6 cycles, at least 7 cycles, at least 8 cycles, at least 9 cycles or at least 10 cycles or more. The administration may occur for as many cycles as necessary to obtain the desired outcome (e.g., remission of the cancer), or until treatments is no longer necessary. For example, the administration may occur for at least 20 cycles, at least 30 cycles, at least 40 cycles, or at least 50 cycles.

In some embodiments, the gedatolisib, or pharmaceutically acceptable salt, solvate, or ester thereof, is administered at a dose of 180 mg once a week. As will be apparent to those of skill in the art, the dose of gedatolisib administered to the subject may be increased or decreased depending on the subject, severity of disease, and mode of administration. For example, the dose of gedatolisib administered may range from about 25 mg per week, 50 mg per week, 100 mg per week, 150 mg per week, or 200 mg per week, up to about 50 mg per week, 100 mg per week, 150 mg per week, 225 mg per week or 250 mg per week.

The methods of described herein may also include administration of additional therapeutic compounds. The additional therapeutic compounds may be administered concurrently with the gedatolisib. Alternatively, the administration of the additional therapeutic compounds can occur asynchronously from the administration of the gedatolisib.

In some embodiments, the method also includes administering a CDK 4/6 inhibitor to the human subject at least once a week for a period of three weeks. The administration of the CDK 4/6 inhibitor is then discontinued for a period of one week, followed by resumed administration of the CDK 4/6 inhibitor for at least one week. The cycle of administration and discontinuation of administration of the CDK 4/6 inhibitor is repeated for at least two cycles.

In some embodiments of the methods of treating cancer, the administering of the CDK 4/6 inhibitor occurs during concurrent weeks as the administration of gedatolisib, or pharmaceutically acceptable salt, solvate, or ester thereof. CDK 4/6 inhibitors that may be useful for the methods herein include, but are not limited to, palbociclib, ribociclib, abemaciclib, trilaciclib, dalpiciclib, riviciclib, and combinations thereof. Preferably, the CDK 4/6 inhibitor is palbociclib. The palbociclib may be administered at dose that produces the desired outcome as determined by the physician. For example, the dose of Palbociclib may be 125 mg per day, 100 mg per day, or 75 mg per day. Preferably, the dose of Palbociclib is 125 mg per day.

Some embodiments of the method of treating cancer include administering an estrogen receptor antagonist to the human subject. Examples of estrogen receptor antagonist that may be used in the methods of the present invention are discussed above. Preferably, the estrogen receptor antagonist is fulvestrant. The fulvestrant may be administered at dose that produces the desired outcome as determined by the physician. For example, the dose of fulvestrant may be 500 mg, or 200 mg, as intramuscular injections, every other week for 6 weeks, (e.g., on days 1, 15, 29) and once monthly thereafter. In some embodiments the fulvestrant administered at a dose of 500 mg every two weeks. In further embodiments the fulvestrant is administered at a dose of 500 mg every four weeks.

A further aspect of the present application relates to a method of treating cancer in a human subject including selecting a human subject in need of treatment of cancer. The method includes administering to the human subject a therapeutically effective amount of gedatolisib, or a pharmaceutically acceptable salt, solvate, or ester thereof, and a CDK 4/6 inhibitor at least once a week for a period of three weeks. This is followed by a period of one week where the administration of the gedatolisib, or pharmaceutically acceptable salt, solvate, or ester thereof, and the CDK 4/6 inhibitor is discontinued. Then the administration of gedatolisib, or pharmaceutically acceptable salt, solvate, or ester thereof, and the CDK 4/6 inhibitor is resumed at least once a week following the period of discontinuation. The administration for at least a period of three weeks and discontinued administration for at least a period of one week constitutes a cycle, and this cycle is repeated for at least two cycles.

In some embodiments, the resumed administration of gedatolisib, or pharmaceutically acceptable salt, solvate, or ester thereof, and the CDK 4/6 inhibitor, occurs at least once a week for a period of three weeks.

Another aspect of the present application relates to a method of treating cancer in a human subject. This method includes selecting a human subject in need of treatment of cancer; administering to the human subject a therapeutically effective amount of gedatolisib, or a pharmaceutically acceptable salt, solvate, or ester thereof, and a CDK 4/6 inhibitor at least once a week for a period of three weeks; discontinuing administration of gedatolisib, or pharmaceutically acceptable salt, solvate, or ester thereof, and the CDK 4/6 inhibitor for a period of one week; resuming administration of gedatolisib, or a pharmaceutically acceptable salt, solvate, or ester thereof, and the CDK 4/6 inhibitor at least once a week following the period of discontinuation, where the administration for at least a period of three weeks and discontinued administration for at least a period of one week constitutes a cycle, wherein the cycle is repeated for at least two cycles; and administering to the human subject an estrogen receptor antagonist.

In some embodiments, the human subject is administered gedatolisib intravenously once weekly for three weeks, followed by one week when gedatolisib is not administered for the treatment of a hormone-dependent cancer (e.g., breast cancer). In some embodiments, the subject has failed a prior treatment (e.g., an endocrine treatment) for breast cancer in a period of less than twelve months (e.g., a period of six months). In some embodiments, the subject has failed two or more prior treatments for cancer. The failed prior treatment(s) may be an endocrine treatment(s) for cancer and/or a non-endocrine treatment(s) or cancer.

The methods of the invention may be used as adjuvant treatment. As used herein "adjuvant treatment" is taken to mean a therapy of a cancer patient immediately following an initial non chemotherapeutical therapy, e.g. surgery, or radiation. In general, the purpose of an adjuvant therapy is to provide a significantly smaller risk of recurrences compared without the adjuvant therapy. For example, the subjects may have surgery or radiation therapy, after which they received treatment using the methods described herein.

The outcomes and efficacy of the methods described herein can be assessed using any suitable method. Symptoms of cancer that may be lessened or eliminated by the methods disclosed herein, include but are not limited to, any subjective, objective or quantitative evidence of disease or other physical abnormality in the subject or patient. For example, the symptoms may include, tumor size, pain, headache, nausea, blood markers indicative of cancer or cancer progression (e.g., CA 15.3, TRU-QUANT, CA 27.29, CA125, CEA (carcinoembryonic antigen), circulating tumor cells), etc.

In some embodiments, the method of treatment results in prolonged progression free survival (PFS), overall survival (OS), and improvements in quality of life.

In some embodiments, the subject achieves a partial response (PR). A partial response may be defined as a reduction in tumor size without achieving complete remission. The reduction in tumor size may allow the subject undergo surgery to remove the tumor.

In some embodiments, the subject achieves a complete response (CR). A complete response may be defined as complete remission of the cancer.

VII. Additional Combination Therapies

In some embodiments, the present invention provides a method of treating cancer including administering to the subject gedatolisib (e.g., according to the dosage regimen described herein) in combination or combined treatment regimen with one or more additional anti-cancer agents. In an embodiment, the anti-cancer agent is a checkpoint inhibitor. In an embodiment, the checkpoint inhibitor is a biologic therapeutic or a small molecule. The checkpoint inhibitor can be a monoclonal antibody, a humanized antibody, a fully human antibody, a fusion protein or a combination thereof. The checkpoint inhibitor may inhibit a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands and combination thereof. The checkpoint inhibitor can interact with a ligand of a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the therapeutic agent is an immunostimulatory agent, a T cell growth factor, an interleukin (e.g., IL-7 or IL-15), an antibody, a vaccine (e.g., dendritic cell (DC) vaccine) or a combination thereof.

In some embodiments, treatment effectivity is determined by a clinical outcome, such as an increase, enhancement or prolongation of anti-tumor activity by T cells; an increase in the number of anti-tumor T cells or activated T cells as compared with the number prior to treatment or a combination thereof. In another aspect, the clinical outcome is tumor stabilization, tumor regression or stabilization; tumor shrinkage; tumor necrosis; anti-tumor response by the immune system; inhibition of tumor expansion, recurrence or spread or a combination thereof.

In a further embodiment, the checkpoint inhibitor and the gedatolisib are administered simultaneously or sequentially, in either order. In an additional embodiment, the gedatolisib is administered prior to the checkpoint inhibitor.

In an embodiment, an additional anti-cancer agent that can be co-administered to the subject is chemotherapeutic agent, e.g., a cytotoxic chemotherapy pharmaceutical compound.

As used herein the term "chemotherapy" or "chemotherapeutic agent" refers to treatment with a cytostatic or cytotoxic agent (i.e., a compound) to reduce or eliminate the growth or proliferation of undesirable cells, for example cancer cells. Thus, as used herein, "chemotherapy" or "chemotherapeutic agent" refers to a cytotoxic or cytostatic agent used to treat a proliferative disorder, for example cancer.

Exemplary cytotoxic chemotherapy pharmaceutical compounds include, but are not limited to, a cyclophosphamide, an ifosamide, a methotrexate, a substituted nucleotide, a substituted nucleoside, fluorouracil, a mitomycin, adriamycin, vincristine, vindesine, taxol, cisplatin, carboplatin, etoposide, or a combination thereof.

In some embodiments, in addition to the gedatolisib, the subject is administered supportive care, for example, pain medication for headaches, treatment for infusion-related reactions (IRRs), and prophylaxis for infusion-related reactions. Symptoms for IRRs include, for example, flushing, alterations in heart rate and blood pressure, dyspnea, bronchospasm, back pain, fever, urticaria, edema, nausea, and rashes.

In some embodiments, treatment for an IRR is selected from the group consisting of: acetaminophen, IV hydration, diphenhydramine, histamine2 blockers (e.g., famotidine), and corticosteroids.

In some embodiments, prophylaxis for IRRs (e.g., if a subject experiences an IRR that requires treatment with corticosteroids) comprises administering hydrocortisone (e.g., hydrocortisone IV) prior to administration of the gedatolisib.

The contents of all figures and all references, Genbank sequences, journal publications, patents, and published patent applications cited throughout this application are expressly incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The following examples are merely illustrative and should not be construed as limiting the scope of this disclosure in any way as many variations and equivalents will become apparent to those skilled in the art upon reading the present disclosure

EXAMPLES

Example 1: Three-Arm Phase 1b Trial of Gedatolisib Plus Palbociclib Plus Fulvestrant in Women with Metastatic Breast Cancer or Locally Advanced/Recurrent Breast Cancer The upregulation of the PI3K/AKT/mTOR pathway promotes hormone dependent and independent ER transcriptional activity, which contributes to endocrine resistance, leading to tumor cell growth, survival, motility, and metabolism. It has also been demonstrated in vivo that PI3K and mTOR inhibition can restore sensitivity to endocrine therapy, providing a strong rationale for the combination of the two therapies. In addition, the PI3K/AKT/mTOR pathway, like other mitogenic pathways, can also promote the activities of cyclin D and CDK4/6 to drive proliferative cell cycling. Internal preclinical studies conducted by Pfizer provided evidence in cell-line xenograft models that the combination of PI3K and CDK4/6 inhibitors may overcome both intrinsic and adaptive resistance to endocrine therapy, leading to tumor regressions. In an MCF7 xenograft model (ER+/HER2−/PIK3CA mutant) the combination of gedatolisib with palbociclib and fulvestrant led to durable tumor regressions. Importantly, tumors regressed to minimal volumes within 20 days of triplet therapy, and continued to remain dormant, without further therapy, for up to 90 days.

To evaluate this hypothesis, Pfizer initiated a Phase 1b trial dose-finding trial with a four-armed expansion portion for safety and efficacy to evaluate gedatolisib when added to either the standard doses of palbociclib plus letrozole or palbociclib plus fulvestrant in patients with ER+/HER2− metastatic breast cancer. PI3K mutation status was not used as an eligibility criterion. Patient enrollment for the trial is complete. A preliminary analysis for the 103 patients enrolled in the expansion portion of the Phase 1b clinical trial, as of the database cutoff date of Jan. 11, 2021, showed:

60% objective response rate (ORR): 53 of the 88 evaluable patients had either a confirmed or unconfirmed partial response, or PR (48 confirmed, 5 unconfirmed).

75% clinical benefit rate (CBR): 66 of the 88 evaluable patients had either a confirmed PR or had stable disease for 24 weeks.

The patients enrolled in Arm D represented the study population that will be enrolled in this tria—patients whose immediate prior therapy was endocrine therapy combined with a CDK4/6 inhibitor.

Median progression free survival was 13.2 months.

This compares to a weighted average median PFS for standard of care therapies of approximately 5.7 months.

1. Objectives

The primary objective of the study was to assess the safety, tolerability, and maximum tolerated dose (MTD) of the triplet combination of gedatolisib added to either the standard dose of the palbociclib/letrozole or palbociclib/fulvestrant. Another objective was to determine if the triplet combination of gedatolisib plus palbociclib/letrozole or gedatolisib plus palbociclib/fulvestrant produces a superior objective response (OR) in patients with metastatic breast cancer (mBC), compared to historical control data of the doublet combination of palbociclib plus either letrozole or fulvestrant.

Secondary objectives included the further assessment of the safety and tolerability of the combinations tested in the study, to assess anti-tumor activity in the dose escalation portion, to assess additional efficacy parameters in the expansion portion, including duration of response (DR) and Progression Free Survival (PFS), to characterize the potential for prolonged QTc interval, to assess the single dose and multiple dose pharmacokinetics (PK) of gedatolisib and palbociclib, and the multiple dose pharmacokinetics of fulvestrant and letrozole (for the Dose Escalation portion only), and to assess the single dose and multiple dose pharmacokinetics (PK) of gedatolisib (for the Dose Expansion portion only).

2. Study Design

This is a Phase 1b, multicenter, open-label, study in patients with mBC. This study has both a dose escalation and expansion portion. The dose escalation portion will identify the MTD of the combination of gedatolisib plus palbociclib/letrozole and gedatolisib plus palbociclib/fulvestrant. The expansion portion will estimate the objective response rate of the combination of gedatolisib plus palbociclib/letrozole and the combination of gedatolisib plus palbociclib/fulvestrant.

The study population for the dose escalation and the dose expansion consists of patients of any menopausal status with ER-positive, HER2-negative, metastatic or locally-recurrent/advanced breast cancer (mBC).

The dose escalation portion of the study initially assess safety and tolerability of the 180 mg/week dose of gedatolisib plus standard doses of palbociclib/letrozole or 180 mg/week dose of gedatolisib plus standard doses of palbociclib/fulvestrant. The dose escalation portion then explore escalating doses of gedatolisib plus each regimen. During the dose escalation 10 DLT evaluable patients are treated at the expected MTD.

Once the MTD of each combination was determined this triggers the initiation of the expansion portion, which comprises 4 arms, as follows: (1) Arm A: first-line endocrine-based therapy; (2) Arm B: second- or third-line endocrine-based therapy, without prior palbociclib (or other CDK inhibitor) therapy; (3) Arm C: second- or third-line endocrine-based therapy with prior exposure to palbociclib (or other CDK inhibitor) therapy, in which gedatolisib is administered once weekly for four weeks; and (4) Arm D: second or third line endocrine based therapy with progression on palbociclib (or other CDK inhibitor) therapy (as the most recent regimen), in which gedatolisib is administered on a three weeks on/one week off (3:1) schedule.

All cycles are 28 days in length. Gedatolisib is administered IV weekly on Days 1, 8, 15 and 22 of each cycle (except for Arm D, in which gedatolisib is administered on Days 1, 8 and 15 of each cycle), palbociclib is administered at 125 mg/day orally continuously dosed for 3 weeks followed by 1 week off, repeated at each subsequent cycle. Letrozole 2.5 mg daily is administered orally on a continuous basis (daily) and fulvestrant is administered at a dose of 500 mg intramuscularly on Cycle 1 Day 1, Cycle 1 Day 15, Cycle 2 Day 1, and then on Day 28 of each subsequent cycle (±3 days).

Treatment continued until progression of disease, uncontrollable toxicity, a decision by the patient or Investigator to discontinue treatment or the study is terminated. Patients experiencing toxicity including a DLT are managed with dose modification or discontinued from treatment.

3. Study Procedures

Safety laboratory tests (hematology, blood chemistry, urinalysis, coagulation) and tumor assessments were done up to 72 hours prior to scheduled Day 1 visit on any cycle to facilitate availability of results to the Investigator at the time of clinic visit.

Other tests and/or increased frequency of examinations or clinical follow up may be needed for patient management depending on findings emerging from the study. The results of these additional tests or examinations are recorded on the case report form (CRY).

Patients are assigned individual trial identification numbers at the time they are approved and registered for enrollment.

Screening assessments must be performed within 28 days (unless otherwise specified) prior to commencing investigational product. Baseline tumor biopsy samples may be archival and if the patient has consented to a fresh tumor biopsy, this must be performed within 28 days prior to the start of investigational product.

As part of the screening/baseline assessment, all patients undergo a complete medical history, including ongoing concomitant medications, clinical assessments (including physical exam, vital signs, height, body weight, ECOG performance status, baseline signs and symptoms, triplicate 12-lead, resting Electrocardiogram [ECG]) and tumor assessments). The required baseline laboratory tests include: blood hematology, coagulation and chemistry, HbA1c, pregnancy test, and urinalysis.

Documentation of tumor phenotype and genotype includes histological or cytological classification, stage information, tumor grade, histologic subtype, ER/progesterone receptor status, HER2 status, and any known tumor-specific molecular markers. Information was provided regarding the method used for the initial diagnostic biopsy (biopsy site, date of biopsy, type of biopsy). The genomic methodology used to ascertain mutation status was provided. Information was provided for all patients about prior anti-tumor treatment, best response and duration of treatment.

All patients enrolling in this study were asked to provide consent to access archived tumor biopsies and to examine genetic variation in proteins and genes associated with a variety of cell signaling pathways. These include (but are not limited to) the components of the PI3K and other signaling pathways, e.g., PTEN, PIK3CA, PIK3R1, and AKT.

If at baseline an archived biopsy was not available, a fresh tumor biopsy was required prior to study entry. Following completion of the screening assessments and confirmation of eligibility, patients may be enrolled.

Participants received treatment according to their assigned study arm. Treatment continued until disease progression or unacceptable toxicity.

4. Study Drug Administration

Administration of investigational products was performed by an appropriately qualified, Good Clinical Practice (GCP)-trained, and vaccine-experienced member of the study staff (e.g., physician, nurse, physician's assistant, practitioner, pharmacist, or medical assistant) as allowed by local, state, and institutional guidance.

Administration of Gedatolisib

Gedatolisib was administered weekly as an IV infusion over approximately 30 minutes. (Dose Escalation; Dose Expansion: Arm A, Arm B and Arm C).

In Arm D of the Dose Expansion portion, gedatolisib was administered on a 3 week on/one week off schedule as an IV infusion over approximately 30 minutes. No premedication was required.

Administration of Palbociclib

Patients were instructed to swallow palbociclib capsules whole and not to manipulate or chew them prior to swallowing. No capsule should be ingested if it is broken, cracked, or otherwise not intact. Patients were encouraged to take their dose at approximately the same time each day. Patients were instructed to record daily administration in the patient diary, and to take palbociclib with food. Palbociclib was administered orally once a day for 21 days followed by 7 days off treatment for each 28-day cycle.

Administration of Letrozole

The recommended dose of letrozole is one 2.5 mg tablet administered once a day, with or without meals.

Administration of Fulvestrant

Fulvestrant requires a loading dose during the first month of treatment. Doses of fulvestrant (500 mg) are given on Day 1, Day 15, and on Cycle 2 Day 1 (in order to accommodate PK schedule. Thereafter, monthly doses are given on Day 28 of subsequent cycles (±3 days).

Injections of fulvestrant are given as intramuscular (IM) injections. A 500-mg dose is given as two injections of 250 mg each, one into each buttock slowly (1-2 minutes per injection) as one 5 mL injection.

5. Endpoints

The coprimary efficacy endpoints of the study were (1) first cycle Dose-Limiting Toxicities (DLTs); and (2) Objective response (OR) as assessed by the Investigator.

The secondary efficacy endpoints of the study were:
1) Safety including adverse events as characterized by type, frequency, severity, timing, seriousness and relationship to study therapy and laboratory abnormalities as characterized by type, frequency, severity and timing.
2) Tumor response for the dose escalation portion of the study.
3) DR and PFS (as assessed using the RECIST v 1.1) for the expansion portion of the study.
4) QTc interval.
5) Single and multiple dose PK parameters of gedatolisib and palbociclib. Multiple dose PK parameters of fulvestrant and letrozole (Dose Escalation portion only).
6) Single and multiple dose PK parameters of gedatolisib (Dose Expansion portion only).

7. Results

Arm D patients received gedatolisib (180 mg IV three weeks on/one week off). It was found upon analysis of the data that synchronizing the treatment schedule for gedatolisib with palbociclib's three week on/one week off schedule was more efficacious in patients who had not received significant benefit from prior treatment with endocrine therapy. This was determined by analyzing the objective response rate and duration of treatment between those patients who failed their prior endocrine treatment in <12 months who received gedatolisib on a weekly schedule (Arm C) versus those who received gedatolisib on a 3 weeks on/1 week off schedule (Arm D). A subset of this patient population (subjects who failed prior treatment in <6 months) was also analyzed. Twenty patients in Arm C and eleven patients in D progressed on their immediate prior therapy in ≤12 months. The median duration of treatment on immediate prior therapy for these patients was essentially the same (146 days vs. 155 days). Of these patients, 15% in Arm C and 73% in Arm D reported a partial objective response. The median duration of treatment on gedatolisib, palbociclib, and fulvestrant for the Arm C patients was 131 days whereas the median duration of treatment in the Arm D patients was 276 days, or more than two times longer than Arm C. The median duration of treatment with gedatolisib compared to immediate prior therapy was 0.9 in Arm C and 1.8 times in Arm D. Twelve patients in Arm C and seven patients in D progressed on their immediate prior therapy in ≤6 months. The median duration of treatment on immediate prior therapy for these patients was essentially the same (97 vs. 106 days). Of these patients, 0% in Arm C and 71% in Arm D reported a partial objective response. The median duration of treatment on gedatolisib, palbociclib, and fulvestrant for the Arm C patients was only 81 days whereas the median duration of treatment in the Arm D patients was 270 days, or more than 3 times longer than Arm C. The median duration of treatment with gedatolisib compared to immediate prior therapy was only 0.8 in Arm C and 2.6 times in Arm D. The results are summarized in Table 1.

TABLE 1

Comparison of Gedatolisib Administered Weekly vs Gedatolisib Administered Cyclically for Patients Who Failed Prior Treatment in Less Than 12 Months

| Arm | Patients with Duration of Immediate Prior Treatment (DIPT) < 180 Days | | Patients with Duration of Immediate Prior Treatment (DIPT) < 365 Days | |
| --- | --- | --- | --- | --- |
| | C | D | C | D |
| # Evaluable patients (% of evaluable) | 12 (44%) | 7 (27%) | 20 (74%) | 11 (42%) |
| Gedatolisib Dosing Schedule | Weekly | 3 weeks on/ 1 week off | Weekly | 3 weeks on/ 1 week off |
| Median DIPT (days) | 97 | 106 | 146 | 155 |
| Median Duration of Gedatolisib (DGT) Treatment (days) | 81 | 270 | 131 | 276 |
| Ratio of median DIPT vs. DGT | 0.8 | 2.6 | 0.9 | 1.8 |
| Overall Response Rate (95% CI) | 0% (0%-25%) $p = 0.0018$ | 71% (36%-92%) | 15% (5%-36%) $p = 0.0011$ | 73% (43%-90%) |

As can be seen from the data presented in Table 1, there is an advantage for subjects who have failed their previous treatment in a period of less than 12 months (e.g., less than 6 months), to receive a three weeks on, one week off cyclic dosing schedule of gedatolisib (Arm D). When compared to weekly administration of gedatolisib (Arm C), the Arm D group reported a higher partial objective response and had a median duration of treatment twice that of the Arm C group.

The benefits of the three weeks on, one week off cyclic dosing schedule of gedatolisib were also seen in patients who had failed two or more prior lines of therapy for cancer. The patients in Arm D were 2.4 times more likely to obtain an objective response (a 30% or greater reduction in tumor mass) and experienced a 2.28 times longer period when their tumor had not progressed (progression free survival) than the patients in Arm C. The results of this patient population analysis are summarized in Table 2.

TABLE 2

Comparison of Gedatolisib Administered Weekly vs Gedatolisib Administered Cyclically for Patients Who Failed 2 or More Prior Lines of Therapy

|  | Arm C | Arm D |
| --- | --- | --- |
| # Evaluable patients | 19 | 9 |
| Gedatolisib Dosing Schedule | Weekly | 3 weeks on/ 1 week off |
| # of Partial Responses | 6 | 7 |
| Objective Response Rate | 32% | 78% |
|  | Odds Ratio = 2.44 | |
|  | p = 0.0418 | |
| Mean Progression Free Survival | 233 | 531 |
|  | Odds Ratio = 2.28 | |
|  | p = 0.00697 | |

The conventional approach to determining the dosing schedule for a therapeutic regimen for cancer patients is to determine the maximum tolerated dose in a Phase 1 clinical trial. This approach is based on the rationale that the efficacy of a cancer therapeutic is directly correlated with the amount of drug administered. Reductions in the dose of therapeutic administered is thus typically motivated by the need to improve the patients' tolerability of the drug. In this example, however, gedatolisib unexpectedly demonstrated superior efficacy when the dosage administered was less than the maximum tolerated dose (180 mg weekly).

It will be understood by those of skill in the art that numerous and various modifications can be made without departing from the scope and spirit of the present disclosure. Therefore, it should be understood that various embodiments of the invention described herein are illustrative only and not intended to limit the scope of the invention. All references cited herein are hereby incorporated by reference in their entirety.

We claim:

1. A method of treating ER+/HER2− breast cancer in a human subject who is being or has been treated with a hormonal therapy, said method comprising:
   administering to the human subject (i) gedatolisib, or a pharmaceutically acceptable salt, solvate, or ester thereof, at a dosage of 180 mg/week, once a week for a period of three weeks; and (ii) a therapeutic dosage of a CDK 4/6 inhibitor for a period of three weeks;
   discontinuing administration of gedatolisib, or pharmaceutically acceptable salt, solvate, or ester thereof, and the CDK 4/6 inhibitor for a period of one week; and
   resuming administration of (i) gedatolisib, or pharmaceutically acceptable salt, solvate, or ester thereof, at a dosage of 180 mg/week once a week and (ii) the CDK 4/6 inhibitor at a therapeutic dosage following the period of discontinuation,
   wherein the administration for a period of three weeks and discontinued administration for a period of one week constitutes a cycle, wherein the cycle is repeated for at least two cycles; and
   wherein the administration of the CDK 4/6 inhibitor occurs during concurrent weeks as the administration of gedatolisib, or pharmaceutically acceptable salt, solvate, or ester thereof.

2. The method of claim 1, wherein resumed administration of (i) gedatolisib, or pharmaceutically acceptable salt, solvate, or ester thereof, occurs at a dosage of 180 mg/week once a week for a period of three weeks; and (ii) the CDK 4/6 inhibitor occurs at a therapeutic dosage for a period of three weeks.

3. The method of claim 1, wherein the cycle of administration occurs for at least 3 cycles, at least 4 cycles, at least 5 cycles, at least 6 cycles, at least 7 cycles, at least 8 cycles, or at least 9 cycles.

4. The method of claim 1, wherein the CDK 4/6 inhibitor is selected from the group consisting of palbociclib, ribociclib, abemaciclib, trilaciclib, dalpiciclib, riviciclib, and combinations thereof.

5. The method of claim 1, wherein the CDK 4/6 inhibitor is palbociclib.

6. The method of claim 5, wherein the palbociclib is administered at a dose of 125 mg per day.

7. The method of claim 1, further comprising administering hormonal treatment to the human subject.

8. The method of claim 7, wherein hormonal treatment comprises administering the estrogen receptor antagonist fulvestrant.

9. The method of claim 8, wherein the fulvestrant is administered at a dose of 500 mg every two weeks.

10. The method of claim 8, wherein the fulvestrant is administered at a dose of 500 mg every four weeks.

11. The method of claim 1, wherein the human subject is a pre-menopausal or post-menopausal female patient.

12. The method of claim 1, wherein the human subject has failed a prior treatment for cancer in a period of less than twelve months.

13. The method of claim 1, wherein the human subject has failed a prior treatment for cancer in a period of less than six months.

14. The method of claim 1, wherein the human subject has failed two or more prior treatments for cancer.

15. The method of claim 12, wherein the failed prior treatment is an endocrine treatment for cancer.

16. The method of claim 7, wherein hormonal treatment comprises administering an aromatase inhibitor.

17. The method of claim 16, wherein the aromatase inhibitor is letrozole.

18. The method of claim 17, wherein letrozole is administered at a dosage of 2.5 mg daily.

19. A method of treating ER+/HER2− breast cancer in a human subject who is being or has been treated with a hormonal therapy, said method comprising:
   administering to the human subject: (i) gedatolisib, or a pharmaceutically acceptable salt, solvate, or ester thereof, at a dosage of 180 mg/week once a week for a period of three weeks; and (ii) a CDK 4/6 inhibitor at a therapeutic dosage for a period of three weeks, wherein the CDK 4/6 inhibitor is selected from the from the group consisting of palbociclib, ribociclib, abemaciclib, trilaciclib, dalpiciclib, riviciclib;

discontinuing administration of gedatolisib, or pharmaceutically acceptable salt, solvate, or ester thereof, and the CDK 4/6 inhibitor for a period of one week; and resuming administration of (i) gedatolisib, or pharmaceutically acceptable salt, solvate, or ester thereof, at a dosage of 180 mg/week once a week and (ii) the CDK 4/6 inhibitor at a therapeutic dosage following the period of discontinuation, wherein the administration for a period of three weeks and discontinued administration for a period of one week constitutes a cycle, wherein the cycle is repeated for at least two cycles; and wherein the administration of the CDK 4/6 inhibitor occurs during concurrent weeks as the administration of gedatolisib, or pharmaceutically acceptable salt, solvate, or ester thereof.

20. The method of claim 19, wherein the CDK 4/6 inhibitor is palbociclib.

21. The method of claim 20, wherein palbociclib is administered at a dose of 125 mg per day.

22. The method of claim 19, wherein the hormonal therapy comprises treatment with letrozole or fulvestrant.

23. The method of claim 19, wherein the cycle of administration occurs for at least 3 cycles, at least 4 cycles, at least 5 cycles, at least 6 cycles, at least 7 cycles, at least 8 cycles, or at least 9 cycles.

24. A method of treating ER+/HER2− breast cancer in a human subject, the method comprising:

administering to the human subject: (i) gedatolisib, or a pharmaceutically acceptable salt, solvate, or ester thereof, at a dosage of 180 mg/week once a week for a period of three weeks; (ii) a CDK 4/6 inhibitor at a therapeutic dosage for a period of three weeks, wherein the CDK 4/6 inhibitor is selected from the from the group consisting of palbociclib, ribociclib, abemaciclib, trilaciclib, dalpiciclib, riviciclib; and (iii) a hormonal therapy selected from fulvestrant and letrozole;

discontinuing administration of gedatolisib, or pharmaceutically acceptable salt, solvate, or ester thereof, and the CDK 4/6 inhibitor for a period of one week; and resuming administration of (i) gedatolisib, or pharmaceutically acceptable salt, solvate, or ester thereof, at a dosage of 180 mg/week once a week and (ii) the CDK 4/6 inhibitor at a therapeutic dosage following the period of discontinuation, wherein the administration for a period of three weeks and discontinued administration for a period of one week constitutes a cycle, wherein the cycle is repeated for at least two cycles; and wherein the administration of the CDK 4/6 inhibitor occurs during concurrent weeks as the administration of gedatolisib, or pharmaceutically acceptable salt, solvate, or ester thereof.

25. The method of claim 24, wherein the CDK 4/6 inhibitor is palbociclib.

26. The method of claim 25, wherein palbociclib is administered at a dose of 125 mg per day.

27. The method of claim 24, wherein fulvestrant is administered at a dose of 500 mg every two weeks.

28. The method of claim 24, wherein letrozole is administered at a dosage of 2.5 mg daily.

29. The method of claim 24, wherein the cycle of administration occurs for at least 3 cycles, at least 4 cycles, at least 5 cycles, at least 6 cycles, at least 7 cycles, at least 8 cycles, or at least 9 cycles.

* * * * *